(12) United States Patent
Helm, Jr.

(10) Patent No.: US 8,715,242 B2
(45) Date of Patent: May 6, 2014

(54) SNAP-SEAL STERILE INTRAVASCULAR CATHETER-DRESSING SYSTEM

(76) Inventor: Robert E. Helm, Jr., Rye Beach, NH (US)

( * ) Notice: Subject to any disclaimer, the term of this patent is extended or adjusted under 35 U.S.C. 154(b) by 66 days.

(21) Appl. No.: 13/349,909

(22) Filed: Jan. 13, 2012

(65) Prior Publication Data

US 2012/0197204 A1  Aug. 2, 2012

Related U.S. Application Data

(60) Provisional application No. 61/437,862, filed on Jan. 31, 2011, provisional application No. 61/482,124, filed on May 3, 2011, provisional application No. 61/482,564, filed on May 4, 2011.

(51) Int. Cl.
*A61M 5/178* (2006.01)
*A61M 5/32* (2006.01)
*A61M 5/00* (2006.01)

(52) U.S. Cl.
USPC ............... 604/164.04; 604/263; 604/164.12; 604/180

(58) Field of Classification Search
USPC ............. 604/164.04, 164.08, 174, 177, 179, 604/180, 263, 905
See application file for complete search history.

(56) References Cited

U.S. PATENT DOCUMENTS

| | | |
|---|---|---|
| 3,683,911 A | 8/1972 | McCormick |
| 3,918,446 A | 11/1975 | Buttaravoli |
| 4,327,723 A | 5/1982 | Frankhouser |
| 4,392,853 A | 7/1983 | Muto |
| 4,464,178 A | 8/1984 | Dalton |
| 4,515,592 A | 5/1985 | Frankhouser |
| 4,551,136 A | 11/1985 | Mandl |
| 4,551,137 A | 11/1985 | Osborne |

(Continued)

FOREIGN PATENT DOCUMENTS

| | | |
|---|---|---|
| DE | 3140192 A1 | 4/1983 |
| WO | 94/05239 A1 | 3/1994 |
| WO | 9702848 A1 | 1/1997 |
| WO | 2008117078 A1 | 10/2008 |

OTHER PUBLICATIONS

International Search Report and Written Opinion mailed Aug. 17, 2012 for Application No. PCT/US2012/021196 (12 Pages).

(Continued)

*Primary Examiner* — Laura Bouchelle
*Assistant Examiner* — Leah Stohr
(74) *Attorney, Agent, or Firm* — Thomas J. Engellenner; Reza Mollaaghababa; Pepper Hamilton LLP

(57) ABSTRACT

Devices and methods are provided for inserting a sterile catheter, and for maintaining a sterilely sealed catheter and catheter insertion site over time. In one embodiment, a four-part integrated system is provided that includes (1) a novel vascular catheter with integrated uniform diameter mounting, capping, and needle safety procurement features, (2) a novel vascular catheter dressing designed to specifically mate with and seal to this vascular catheter to achieve a sterile seal both at the catheter-skin insertion site and the catheter-dressing exit site, (3) a hub protection and sterilizing apparatus that serves to stabilize, protect, and sterilize the working end of the catheter hub as it protrudes from the sterile dressing, and that also helps to improve the ergonomics of the catheter-dressing complex in order to avoid snagging on clothing etc., and (4) a whole dressing accessory secondary cover and securement device.

24 Claims, 19 Drawing Sheets

(56) References Cited

U.S. PATENT DOCUMENTS

| | | |
|---|---|---|
| 4,563,177 A | 1/1986 | Kamen |
| 4,634,433 A | 1/1987 | Osborne |
| 4,767,411 A | 8/1988 | Edmunds |
| 4,781,695 A | 11/1988 | Dalton |
| 4,966,590 A | 10/1990 | Kalt |
| 5,074,847 A | 12/1991 | Greenwell |
| 5,112,313 A | 5/1992 | Sallee |
| 5,116,324 A | 5/1992 | Brierley et al. |
| 5,215,532 A | 6/1993 | Atkinson |
| 5,232,453 A | 8/1993 | Plass et al. |
| 5,238,010 A | 8/1993 | Grabenkort et al. |
| 5,336,195 A | 8/1994 | Daneshvar |
| 5,344,415 A | 9/1994 | DeBusk et al. |
| 5,372,589 A | 12/1994 | Davis |
| 5,380,294 A | 1/1995 | Persson |
| 5,415,642 A | 5/1995 | Shepherd |
| D359,120 S | 6/1995 | Sallee et al. |
| 5,478,326 A | 12/1995 | Shiu |
| 5,527,277 A | 6/1996 | Ensminger et al. |
| 5,577,516 A | 11/1996 | Schaeffer |
| 5,685,865 A | 11/1997 | Cosgrove et al. |
| 5,686,096 A | 11/1997 | Khan et al. |
| 5,690,612 A | 11/1997 | Lopez et al. |
| 5,694,686 A | 12/1997 | Lopez |
| 5,702,371 A | 12/1997 | Bierman |
| 5,707,348 A | 1/1998 | Krogh |
| 5,715,815 A | 2/1998 | Lorenzen et al. |
| 5,722,959 A | 3/1998 | Bierman |
| 5,769,807 A | 6/1998 | Haddock et al. |
| 5,772,636 A * | 6/1998 | Brimhall et al. ............ 604/198 |
| 5,776,106 A * | 7/1998 | Matyas ...................... 604/180 |
| 5,807,341 A | 9/1998 | Heim |
| 5,820,607 A | 10/1998 | Tcholakian |
| 5,989,220 A | 11/1999 | Shaw et al. |
| 6,080,138 A | 6/2000 | Lemke et al. |
| 6,099,509 A | 8/2000 | Brown, Jr. et al. |
| 6,132,399 A | 10/2000 | Shultz |
| 6,302,867 B1 | 10/2001 | Brown, Jr. et al. |
| 6,375,639 B1 | 4/2002 | Duplessie et al. |
| 6,413,240 B1 | 7/2002 | Bierman et al. |
| 6,569,121 B1 | 5/2003 | Purow et al. |
| 6,571,395 B1 | 6/2003 | Korkor |
| 6,809,230 B2 | 10/2004 | Hancock et al. |
| 6,827,707 B2 | 12/2004 | Wright |
| 7,083,598 B2 | 8/2006 | Liska |
| 7,153,291 B2 | 12/2006 | Bierman |
| 7,244,245 B2 | 7/2007 | Purow et al. |
| 7,247,150 B2 | 7/2007 | Bierman |
| 7,544,186 B2 | 6/2009 | Davis et al. |
| 7,578,804 B2 | 8/2009 | Bierman |
| 7,723,561 B2 | 5/2010 | Propp |
| 7,744,572 B2 | 6/2010 | Bierman |
| 7,799,001 B2 | 9/2010 | Bierman |
| 7,806,873 B2 | 10/2010 | Dikeman et al. |
| 2002/0082559 A1 | 6/2002 | Chang et al. |
| 2002/0092529 A1 | 7/2002 | Rozier et al. |
| 2003/0078540 A1 | 4/2003 | Saulenas |
| 2005/0065479 A1 | 3/2005 | Schiller |
| 2005/0113798 A1 | 5/2005 | Slater et al. |
| 2005/0261623 A1 | 11/2005 | Propp |
| 2006/0030820 A1 | 2/2006 | Alheidt |
| 2006/0211994 A1 | 9/2006 | Roman et al. |
| 2006/0247577 A1 | 11/2006 | Wright |
| 2006/0247582 A1 | 11/2006 | Alheidt |
| 2006/0264836 A1 | 11/2006 | Bierman |
| 2007/0027429 A1 | 2/2007 | Kuracina et al. |
| 2007/0055205 A1 | 3/2007 | Wright et al. |
| 2007/0060892 A1 | 3/2007 | Propp |
| 2008/0058692 A1 | 3/2008 | Propp et al. |
| 2008/0125750 A1 | 5/2008 | Gaissert |
| 2008/0221531 A1 | 9/2008 | Alheidt |
| 2008/0262439 A1 | 10/2008 | Alheidt |
| 2009/0118696 A1 | 5/2009 | Nyhart, Jr. |
| 2009/0192470 A1 | 7/2009 | Propp |
| 2009/0306602 A1 | 12/2009 | Elwell et al. |
| 2010/0100049 A1 | 4/2010 | Godfrey |
| 2010/0179482 A1 | 7/2010 | Wright et al. |
| 2011/0106014 A1 | 5/2011 | Helm, Jr. |
| 2012/0232489 A1 | 9/2012 | Helm |
| 2013/0178825 A1 | 7/2013 | Helm, Jr. |

OTHER PUBLICATIONS

Alibaba.com Product Literature—IV Catheter Dressing (accessed Nov. 17, 2010).

Become.com Product Literature—3m Catheter Dressing (accessed Nov. 17, 2010).

Clemens, Mary, New IV Dressing Benefits Both the Patient and Clinician, Reuters.com, Feb. 2, 2009.

David C. McGee, M.D. and Michael K. Gould, M.D., Preventing Complications of Central Venous Catheterization, N Engl J Med 2003; 348:1123-1133.

Dr. Maree Johnson, Systematic Review Central Line Dressing Type and Frequency, Joanna Briggs Institute, Jan. 20, 1998.

International Search Report, PCT/US10/054427, dated Jul. 20, 2011.

IV Team, BD Announces UK Launch of new BD Nexiva(TM) Closed IV Catheter System Designed to Help Protect Healthcare Workers, PR Newswire.com, Jul. 29, 2009.

Maki DG, and Ringer M., Evaluation of dressing regimens for prevention of infection with peripheral intravenous catheters. Gauze, a transparent polyurethane dressing, and an iodophor-transparent dressing., JAMA. Nov. 6, 1987;258 (17):2396-403., pubmed.gov.

Seattle Treatment Education Project, The Body, The Facts About Intravenous Catheter Lines, thebody.com, Oct. 1992.

Silverlon® "Lifesaver• Ag" 7 Day Antimicrobial IV/Catheter Dressing Product Literature, silverlon.com (accessed Nov. 17, 2010).

Smith & Nephew Product Literature—I.V. and Catheter Sites, smith-nephew.com (accessed Nov. 17, 2010).

Sorbaview Shield Product Literature, centurionmp.com (accessed Nov. 17, 2010).

Walgreens.com Product Literature—Medline Suresite I.V. Transparent Catheter Dressing 2×3 (accessed Nov. 17, 2010).

Written Opinion of International Searching Authority, PCT/US10/054427, dated Jul. 20, 2011.

Australian Office Action issued Nov. 1, 2012 for Application No. 2010319924 (3 Pages).

Supplemental European Search Report mailed Apr. 18, 2013 for Application No. 10830440.3 (7 Pages).

International Preliminary Report on Patentability for Application No. PCT/US2010/054427 mailed May 10, 2012 (7 Pages).

Australian Office Action issued Jun. 20, 2012 for Application No. 2010319924 (5 Pages).

* cited by examiner

B-B

B-B

A-A

SNAP-SEAL STERILE INTRAVASCULAR CATHETER-DRESSING SYSTEM

CROSS-REFERENCE TO RELATED APPLICATIONS

This application claims the benefit of priority of U.S. Provisional Patent Application No. 61/437,862, filed on Jan. 31, 2011, the entire contents of which are incorporated herein by reference. This application also claims the benefit of priority of U.S. Provisional Patent Application No. 61/482,124, filed on May 3, 2011, the entire contents of which are incorporated herein by reference. This application also claims the benefit of priority of U.S. Provisional Patent Application No. 61/482,564, filed on May 4, 2011, the entire contents of which are incorporated herein by reference.

FIELD

The present invention relates to methods and devices for sterilely sealing and securing medical devices, and in particular to methods and devices for inserting, sealing, and maintaining sterility of an intravascular catheter and its insertion site.

BACKGROUND

Much attention has been paid, in both the medical literature and lay press, to the general issue of healthcare-related infection. The alarming increase in multi-drug resistant organisms, combined with the well-documented costs of treating healthcare-associated infections, has led to a strong worldwide mandate to address and eliminate all potential avenues for infection. Driving these efforts further is the decision by the United States Centers for Medicare and Medicaid Services to no longer reimburse hospitals for costs that can be related to healthcare-acquired infection. Prominent among the listed adverse events that will no longer be covered are all catheter-related infections. Arising from the consequent strong drive by hospitals and the health care system to eliminate catheter-related infection, multiple new procedures and products have been introduced. These have included antibiotic-impregnated dressings and catheters, antibiotic-impregnated dressing adjuncts, catheter access point cleansing devices, and the application of new rigorous catheter care guidelines. Despite these efforts, catheter-related infections continue.

All existing vascular catheter dressings rely on a simple Band-Aid® type covering mechanism that presses the catheter flat against the skin. Two types of such dressings are currently recommended by the United States Centers for Disease Control and Prevention: one consisting of gauze and tape, and the second consisting of a self-adhesive film. While the dressing material itself may be sterile at first, its inability to seal at the catheter-dressing exit point precludes maintenance of this sterility. The result is the need to change the catheter dressing to a new clean dressing at frequent intervals. The catheters themselves must also be removed at specified intervals, and new catheters placed. Additionally, any movement of the catheter loosens the dressing, compounding sterility issues. Water and contaminating fluids have direct access to the catheter and its insertion site. Catheter movement and non-sterility can lead to other complications such as thrombophlebitis as well.

In addition to the adverse sequelae of infection and thrombophlebitis—as well as caregiver inefficiency and patient discomfort resulting from catheter and dressing changes— other problems continue to plague current catheter and catheter care systems. First, compounding the fundamental problem of inadequate dressing structure, is the tremendous variability in the methodology for placing traditional catheters and catheter dressings. Catheter placement and care techniques are very user-dependent, both from an institutional and individual caregiver standpoint. Clinically, this leads to an unacceptably high incidence of sub-optimally placed intravascular catheters and intravascular catheter dressings—catheters and dressings that are already fundamentally inadequate by design. Second, adequate sterile securement of vascular catheters continues to be an issue. The two traditional patch type dressings recommended by the CDC only partially secure the catheter, relying on supplemental non-sterile supportive tape or other specifically-applied securement devices that serve to compound the problem of insufficient sterility. Inadvertent pulling out of vascular catheters by patients is not uncommon, and can lead to significant blood loss, unsafe loss of vascular access, and even death.

The fact that new dressing adjuncts have been so quickly-adopted demonstrates both the understanding by the medical-industrial system of the inadequacy of traditional intravascular catheters and dressings, and the thirst by this system for a solution to the problem of catheter-related infection. In the final analysis, however, these compensatory measures are just that—technical and pharmacologic maneuvers that simply compensate for an antiquated and suboptimal approach to vascular catheter placement and care. Clearly, a need exists for improved catheter placement and catheter dressing equipment and techniques.

SUMMARY

Methods and devices for dressing catheters and catheter insertion sites are provided that can minimize or even eliminate catheter-related infection, and can markedly improve health care delivery of vascular catheter care. Integrated catheter-dressing systems are provided that allow for optimal insertion and maintenance of a durably secure, sealed, and sterile vascular catheter. These systems permit a catheter to be placed at any desired percutaneous insertion site, for a sterile, sealed, and secure dressing to be applied to the catheter, for the maintenance of the catheter and catheter insertion site sterility over time, and for ergonomic and sterile protection of the catheter hub connection point when not in use. The catheter-dressing systems disclosed herein also provide for safety insertion needle containment in a manner that integrates with the form and function of the systems. In one embodiment, the system includes (1) a novel vascular catheter, (2) a sterile sealing dressing designed specifically to mate with this novel catheter, (3) a catheter hub sealing and sterilizing device designed to mate with both the novel catheter and the sealing dressing, and (4) a whole catheter-dressing system protective cover. Together, these four components create an easy to use, highly reproducible, and totally comprehensive system for providing a durably sterile, safe and secure intravascular catheter. While these four components can act in an integrated manner as described, they can also be applied individually or in any combination with existing (or future) catheter and dressing technologies.

In one aspect, a catheter system is provided that includes a catheter assembly comprising an implantable catheter and a catheter hub formed at a proximal end of the implantable catheter, a needle containment device extending proximally from the catheter assembly, the needle containment device being coupled to an insertion needle disposed through an inner lumen of the implantable catheter, and a dressing assembly configured to slide over the catheter hub to form a circumferential seal around the catheter hub and a catheter insertion site. The system can also include a hub cap designed to allow insertion of the catheter and placement of the dressing assembly without unnecessary back-bleeding onto the catheter site during placement. This cap can be left in place after appropriate flushing, or it can be replaced with any standard cap device. When included in the integrated catheter-dressing system, this catheter hub cap, like the needle containment device, can have an external diameter less than or equal to the main catheter hub, and less than a stop flange extending from the catheter hub, in order that the sterile dressing assembly can be slid over and past this hub cap component. The system can optionally include a hub protection device that cleans and ergonomically protects the catheter hub and/or an associated hub cap when not in use. The system can also include a protective cover that secondarily secures the catheter-dressing system to the body during periods of activity or prolonged non-use.

The needle containment device can include a tapered or otherwise shaped distal end to facilitate sliding of the dressing assembly from the needle containment device onto the catheter hub. The needle containment device can have an outer diameter that is less than the outer diameter/dimension of a stop flange formed on the catheter hub, or that is less than a stop point formed on existing or modified catheters or connection devices, thereby allowing sliding of the sterile dressing assembly over the needle containment device and onto the connection device or catheter hub and into mounting position. In one embodiment, the needle containment device includes a telescoping portion such that the needle containment device is extendable between a first position in which the insertion needle coupled thereto is fully inserted through the implantable catheter and a second position in which the insertion needle is fully withdrawn from the implantable catheter. In another embodiment, the needle containment device includes an elongate shaft and a slider, the slider being slidable relative to the elongate shaft and being coupled to the insertion needle such that the slider can be placed in a first position in which the insertion needle coupled thereto is fully inserted through the implantable catheter and a second position in which the insertion needle is fully withdrawn from the implantable catheter and secured in a fashion consistent with safe needle handling and disposal practice. The needle containment device can be lockable in at least one of a first position in which the insertion needle coupled thereto is fully inserted through the implantable catheter and a second position in which the insertion needle is fully withdrawn from the implantable catheter. Rotation of the slider relative to the elongate shaft can be effective to lock the insertion needle in a fixed position relative to the needle containment device. The slider can be locked into the desired position by other mechanisms as well, such as by advancing the slider past a specifically-formed circumferential ridge formed at one or more desired stop point(s) and configured so that only one way "locking" movement of the slider past the ridge is allowed.

The catheter assembly can also include a hub cap configured to be selectively coupled to a proximal end of the catheter hub, and the needle containment device can optionally be detachably connected to the hub cap and/or directly to the catheter hub. The hub cap can be in the form of or can include a reversibly-sealable membrane or septum through which the insertion needle of the needle containment device can be selectively passed without disrupting a fluid-tight seal across a proximal end of the hub cap. The insertion needle can first be inserted through the membrane and can subsequently be withdrawn through the membrane during the insertion process, the membrane preventing unwanted back-bleeding or spillage and preserving sterility. The hub cap and the needle containment device can each have a maximum diameter that is less than or equal to a maximum diameter of the catheter hub and less than a maximum diameter of a stop flange extending from the catheter hub. The hub cap can optionally serve as an intermediary between the needle containment device and the catheter during the catheter-dressing insertion process, preventing backflow of blood after the needle is withdrawn into the needle containment device and during the dressing mounting process.

The dressing assembly can include an adhesive base plate, a body portion, and a hub receiving channel formed in the body portion, the hub receiving channel being configured to form a sealing snap-fit engagement with the catheter hub when the catheter hub is disposed therein. In one embodiment, the system can include a hub cap configured to be selectively coupled to a proximal end of the catheter hub, and the hub cap and the needle containment device can each have a maximum outer diameter that is less than or equal to a maximum outer diameter of the catheter hub and less than a maximum outer diameter of a stop flange extending from the catheter hub. At least one of the dressing assembly and the catheter hub can be configured to generate audible and/or tactile feedback to a user when the dressing assembly becomes fully mated to the catheter hub.

The dressing assembly can also include an access portal covered by a closure device. The dressing assembly can also include first and second access portals, each of the first and second access portals being covered by a closure device. In one embodiment, the closure device can include a re-sealable flap. The closure device can include a sterilizing agent impregnated material, which can be attached thereto and can be inserted into a sterile chamber of the dressing assembly by the act of placing a new access portal cover. In another embodiment, a second access portal is available for use in the introduction of additional sterilization materials. This could take the form of, for example, an injection port for antimicrobial solution. In one embodiment, the hub receiving channel of the dressing assembly includes an annular projection formed therein configured to form a sealing snap-fit engagement with a corresponding annular recess formed in the catheter hub. Alternatively, or in addition, the hub receiving channel of the dressing assembly can include a flange-receiving recess formed therein configured to mate with and seal to a corresponding stop flange formed on an exterior of the catheter hub. This stop flange can be used alone or in conjunction with the annular recess on the catheter hub to firmly secure the catheter in place. The stop flange can be configured to prevent rotation of the catheter hub relative to the dressing assembly and to prevent the implantable catheter from being pulled out of the dressing assembly and/or the patient. The stop flange can extend radially-outward from the catheter hub and can have an octagonal cross-section, a hexagonal cross-section, or any of a variety of other cross-sections such as a quadrangular cross-section, a circular cross-section, or an ovoid cross-section. In one embodiment, the stop flange comprises opposed lateral extensions.

In one embodiment, a distance between the annular recess and the stop flange can be less than a distance between the annular projection and the flange-receiving recess such that the stop flange exerts a compressive force on the flange-receiving recess when the dressing assembly is mated to the catheter assembly. The stop flange can have a cross-sectional dimension that is greater than a corresponding cross-sectional dimension of the hub receiving channel such that the stop flange prevents the catheter hub from being pulled proximally out of the dressing assembly. For example, the stop flange can have a larger overall diameter than the remainder of the catheter hub and the main portion of the hub receiving channel, such that the larger diameter acts as a mechanical stop, preventing the catheter hub and the catheter from being pulled proximally out of the dressing assembly. Thus, the interaction between the stop flange and the flange-receiving recess (which can be at the interface between the hub receiving channel and the sterile chamber of the dressing) can prevent the catheter from being pulled out of the dressing (and out of the patient). The flange-receiving recess can be located at the distal end of the hub receiving channel, where the channel interfaces with the sterile chamber of the dressing, such that the stop flange forms a secondary seal at the stop-flange/recess mating point. Audible and/or tactile feedback can optionally be generated upon creation of this secondary seal.

The hub receiving channel and/or the sterile chamber of the dressing can be treated, lined, and/or coated with a sterilizing agent impregnated lining so that during the mounting of the dressing over the catheter system sterility is maintained. Similarly, the access portal window cover can allow placement of—or have integrally attached—a material impregnated with a sterilizing agent.

The shape and interaction of the catheter assembly and the dressing assembly can allow for the lowest possible resting profile of the inserted catheter. In one embodiment, the dressing assembly can be shaped such that the catheter assembly lies substantially flat against a patient when the catheter is inserted into the patient and the dressing assembly is mated to the catheter assembly. In respect to the catheter hub, a hexagonal stop flange or lateral flange design, with minimal downward protrusion (toward the skin) can optimize the catheter's low profile position relative to the skin surface. The dressing assembly can be fixedly mated to the catheter assembly such that manual manipulation of the dressing can be effective to directly stabilize and manipulate the contained catheter hub during use of the hub (e.g., during attachment of intravenous lines). In one embodiment, manual manipulation of the dressing assembly is effective to manipulate the catheter assembly when the catheter assembly is mated to the dressing assembly. In one embodiment, the surface of the dressing can be altered at specific points to allow for optimal manipulation of the contained catheter. These alterations can take the form of indentations, changes in contour, and/or surface textural changes, designed to optimize finger manipulation.

The catheter system can also include a hub protection device having a bore formed therein for receiving at least a portion of the catheter hub or a hub cap coupled to a proximal end of the catheter hub. The bore can include an annular projection formed therein configured to form a sealing snap-fit engagement with a corresponding annular recess formed in the catheter hub. The hub protection device can also include a distal projection configured to mate with a corresponding recess in the dressing assembly. The bore of the hub protection device can be lined with an antibiotic-impregnated material and/or an antimicrobial-impregnated material. The catheter hub can be formed from a semi-rigid or flexible material configured to disperse mechanical forces tending to disrupt the circumferential seal. The hub protection device can include an arcuate upper surface that forms a continuous arc with an arcuate upper surface of the dressing assembly when the hub protection device is coupled to the dressing assembly. The shape of the hub protection device can be designed in conjunction with the shape of the dressing assembly to form the smoothest possible ergonomic arc to minimize catching of the dressing/catheter system on clothing, etc.

The catheter system can also include a protective cover configured to further secure the dressing assembly to a patient, augment a sterile seal formed between the dressing assembly and the patient, and/or promote longevity of the sterile state. The protective cover can be used when a patient is engaged in activities that would otherwise threaten the integrity of the catheter-dressing system. This protective cover can be applied over the dressing assembly, and then secured to the patient's body by various means appropriate to that body part. For example, an elastic arm band with a Velcro-type closure could be employed when the dressing is placed on a patient's arm. The protective cover can protect the catheter-dressing system and also augment the integrity of its adhesive seal. The protective cover can be particularly useful in pediatric patients, or in those with altered mental status, during periods of prolonged non-use, during activity, and/or during any other period of increased withdrawal risk. In one embodiment, the protective cover can be formed from a rigid or semi-rigid plastic that is fit-molded to the shape of the dressing.

In one embodiment, the dressing assembly can include a vacuum port through which a vacuum can be applied to an interior volume of the dressing assembly. The catheter system can also include a balloon disposed within the dressing assembly, the balloon being operatively coupled to an inflation lumen accessible from an exterior of the dressing assembly when the dressing assembly is mated to a skin surface. Inflation of the balloon can be effective to exert pressure on the skin surface.

In another aspect, a kit is provided that can include any of the catheter systems disclosed herein and at least one of sterile gloves, sterilizing solutions, sterilizing solution applicators, tourniquets, sterile flush solutions, and sterile drapes.

In another aspect, a method of placing and dressing an intravascular catheter is provided. The method can include inserting a guide needle through a skin surface of a patient into a blood vessel, the guide needle having a catheter disposed therearound, the catheter being coupled to a needle containment device, and retracting the needle containment device proximally, thereby withdrawing the guide needle from the blood vessel, until the guide needle is contained and, in one embodiment, locked within the needle containment device. The method can also include advancing a circumferentially-sealing dressing assembly distally over the needle containment device and the catheter hub towards the skin surface and sealing the dressing assembly to the catheter hub and to the skin surface.

The method can also include separating the needle containment device and the guide needle from the catheter hub after sealing the dressing assembly. The catheter can include a hub cap and the hub cap can be coupled to the needle containment device. The method can also include, after separating the needle containment device, removing the hub cap or other sterile cover device and attaching at least one of a Luer Lock connector, an Insyte connector, and an intravenous line to the catheter. Various other hub caps or intermediate connection devices can also be attached to the catheter. The method can also include, after separating the needle containment device, installing a hub protection device over a portion of the catheter hub or hub cap protruding from the dressing assembly by coupling the hub protection device to the dressing assembly and to the catheter hub and/or hub cap.

The method can also include manually holding the needle containment device while advancing the dressing assembly (e.g., using the needle containment device as a handle during the sterile dressing insertion process). In one embodiment, sealing the dressing assembly to the catheter hub comprises mating an annular recess formed in the catheter hub with an annular projection formed on the dressing assembly to form a snap-fit engagement. Sealing the dressing assembly to the catheter hub can also include mating a flange formed on the catheter hub with a corresponding recess formed in the dressing assembly.

In one embodiment, the mating of the flange to the corresponding recess prevents longitudinal dislodgement of the catheter from the skin surface. The mating of the flange to the corresponding recess can also prevent rotational movement of the catheter relative to the dressing assembly. The method can also include using the sealed dressing assembly to grasp and manipulate the catheter. The dressing assembly can optionally have formed indentations or other functional formations that denote specific grasping points on the dressing assembly that are optimal for manipulation of the catheter.

The method can also include opening an access portal of the dressing assembly, applying a sterilizing agent to an interior of the dressing assembly, and re-sealing the access portal. The method can also include replacing a cover of the access portal with a new cover. The method can also include the use of a second sterile access portal for injection or application of sterilizing/cleansing agent to allow for optimal extension of the sterile state of the catheter-skin insertion point.

The method can also include placement of a protective cover during periods of activity, in patients at high risk for inadvertent or purposeful catheter removal/dislodgement, and/or during periods of prolonged non-use such as in the outpatient setting. The method can also include the use of a comprehensive sterile catheter insertion and dressing system placement kit that includes various materials for (1) preparation of the body site for catheter insertion (e.g. gloves, sterilizing materials/solutions), (2) insertion and flushing of the catheter, and (3) placement of the sterile dressing. In one embodiment, the skin surface, catheter, guide needle, needle containment device, and/or dressing assembly are sterilized prior to inserting the guide needle through the skin surface and the dressing assembly is placed using sterile technique and equipment (e.g., sterile gloves, sterile surface preparation, draping, etc.).

The method of can also include applying a vacuum to an interior volume of the dressing assembly to draw the dressing assembly against the skin surface and further stabilize the catheter. In one embodiment, the method includes inflating a balloon disposed within the dressing assembly after removing the catheter to apply a compressive force to the skin surface. The method can also include leaving the dressing assembly in place on the skin surface after removing the catheter to maintain sterility during healing of the catheter insertion site.

In another aspect, a dressing assembly is provided that includes an adhesive plate configured to attach to the skin of a patient, the adhesive plate including an aperture through which an external portion of an implanted catheter can be received and a body portion fixedly attached to the adhesive plate, the body portion including a proximal opening configured to be circumferentially sealed to the implanted catheter. The dressing assembly also includes a resealable and replaceable flap portion coupled to the body portion and configured to be selectively peeled away from and attached to the body portion. The body portion and the flap portion together define a sterile sealed chamber with a skin surface of a patient when the dressing assembly is adhered thereto. In one embodiment, the proximal opening of the body portion can be configured to be circumferentially sealed to a connecting device coupled to a proximal end of the implanted catheter. The connecting device can be at least one of a Luer Lock connector and an Insyte connector. The flap portion can provide an access portal for accessing the sterile sealed chamber.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while methods and devices are described herein in connection with catheters implantable in humans, the methods and devices can also be used in any instance in which a seal is desired around an elongate device implanted into or otherwise extending from a plant, an animal, and/or any non-living machine, structure, or system. In addition, while the methods and devices disclosed herein are described primarily with respect to intravenous catheters, they can also be used with any of a variety of other devices and other procedures including, without limitation, arterial monitoring lines, access sheaths for intravascular procedures such as angiography and stenting, access sheaths for intravascular therapeutic devices such as intra-aortic balloon pumps and ventricular support devices, etc.

Figure 1:
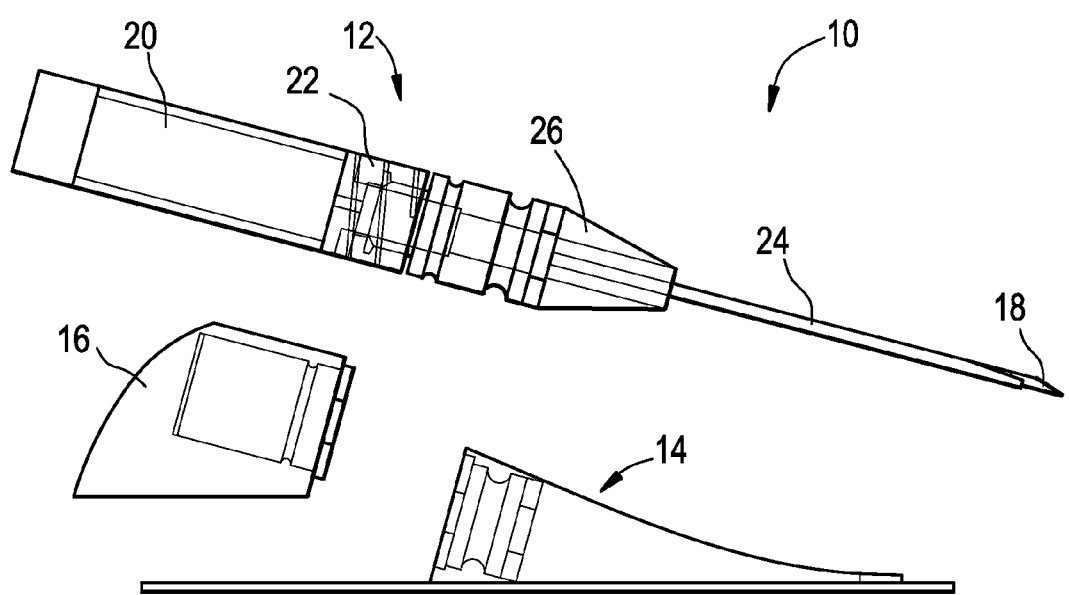
FIG. 1 is a side view of one embodiment of a catheter-dressing system according to the invention.

FIG. 1 illustrates one exemplary embodiment of a snap-fit catheter-dressing system 10 according to the present invention. The system 10 generally includes a catheter assembly 12, a dressing assembly 14, and a hub protection device 16. The catheter assembly 12 can include an insertion needle 18, a needle containment device 20, a hub cap 22, a catheter 24, and a catheter hub 26. In the illustrated embodiment, the needle containment device 20, the hub cap 22, and the catheter hub 26 each have a diameter that is less than the stop flange on the catheter hub, which, as described below, can provide a number of advantages.

Figure 2A:
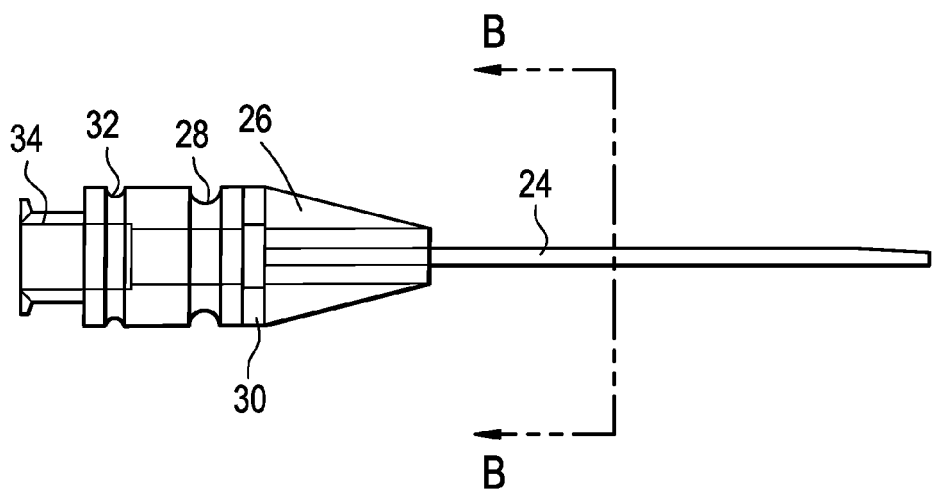
FIG. 2A is a side view of the catheter hub and the catheter of the system of FIG. 1.

As shown in FIG. 2A, the catheter hub 26 extends from the proximal end of the catheter 24. The elongated, custom-shaped hub 26 can include any of a variety of features to enable it to integrate with the other components of the catheter-dressing system 10. In particular, hub 26 allows for the dressing assembly 14 to be applied over, and attached in sealing engagement to, the hub 26 after the catheter 24 has been inserted. The length of the hub 26 can be minimized to just that which is needed to provide for optimal catheter securement, sealing, and manipulation. The customized hub length and shape can advantageously allow for the creation/existence of various sealing and securing mechanisms formed along the exterior of the hub 26. The size and shape of the hub 26 can also permit appropriate manual manipulation of the hub 26 during application of the sterile dressing assembly 14 and manipulation of the catheter 24 through the attached dressing assembly 14 once the dressing assembly 14 has been applied (e.g., for the purpose of attaching IV lines to the catheter 24, etc.). The length of the hub 26 can also be selected such that the hub 26 extends or protrudes proximally past the dressing assembly 14 to facilitate use of the catheter 24 (e.g., attachment of IV lines thereto).

The hub 26 can have a uniform maximum outer diameter that allows sealing application of the sterile dressing assembly 14 over the inserted catheter hub 26. The hub 26 can be made of rigid, semi-rigid, or flexible material. A hub constructed of semi-rigid or flexible material, for example, can advantageously allow for the dissipation of force vectors that could otherwise serve to lift and loosen the sterile dressing assembly 14. The hub 26 can also be transparent or semi-transparent to allow visualization of blood contained therein (e.g., for the purpose of confirming intravascular placement or confirming adequate flushing of blood from the catheter 24).

The hub 26 can also be provided with a snap-fit type sealing mechanism that provides a sterile seal with the dressing assembly 14 and fixes the dressing assembly 14 in place relative to the catheter 24 (and vice versa). This mechanism can be constructed such that the uniform outer diameter of the hub 26 is maintained. This sealing/mating point can be designed to custom bind to the sterile dressing assembly 14. In one embodiment, this mating point is a ringed depression 28 into which a corresponding protuberance formed in a hub receiving channel of the dressing assembly 14 snap-fits.

Figure 2B:
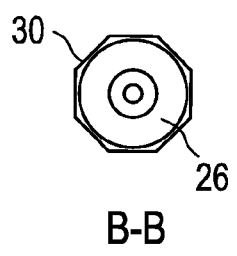
FIG. 2B is an end view of one embodiment of a catheter hub stop flange.
Figure 2C:
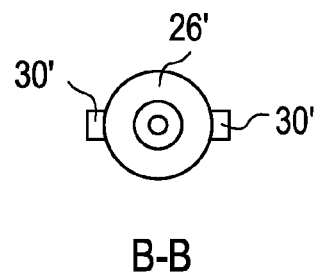
FIG. 2C is an end view of another embodiment of a catheter hub stop flange.

A distal inner stop flange 30 can be provided on the catheter hub 26 to engage a corresponding female recess formed in the hub receiving channel of the dressing assembly 14. This flange 30 can help prevent inadvertent pulling out of the catheter 24 relative to the dressing assembly 14 and the insertion site, and also to provide rotational fixation of the catheter hub 26 relative to the dressing assembly 14. In addition, the flange 30 can augment the sterile seal created at the dressing assembly/catheter hub interface. The flange 30 can be in the form of an octagon as shown in FIG. 2B, in the form of dual lateral flanges 30' as shown in FIG. 2C, or in the form of some other shape such as a hexagon or square. The lateral flange design 30' can be designed to allow for a lower profile resting angle for the inserted catheter 24, which can be desirable in some cases. The flange can snap into place by itself at the corresponding recess point on the dressing, or in conjunction with the annular mating point at the catheter-dressing interface.

Together, the snap fit seal formed at the recess 28 and the seal formed at the flange 30 optimally seal and secure the catheter 24 to the sterile dressing assembly 14. As discussed further below, the dressing assembly 14 can be simultaneously adhered to the patient's skin circumferentially around the catheter insertion site, thus securing the dressing assembly 14 and the catheter 24 to the patient. Accordingly, longitudinal and rotational movement of the catheter 24 relative to the patient/blood vessel is prevented, which can increase patient comfort and minimize the risk of trauma-related thrombophlebitis.

The catheter hub 26 can also include an attachment and/or positioning mechanism for the hub protection device 16. This can be in the form of a snap-fit mating member (e.g., an annular depression 32), similar to that used to attach the catheter hub 26 to the sterile dressing assembly 14. To avoid premature fixation of the dressing assembly 14 to this site (e.g., the annular depression 32) when sliding the dressing assembly 14 over the catheter hub 26 during initial placement, this first encountered groove 32 can be made narrower than the snap-fit groove 28 meant for the dressing assembly 14.

The hub 26 can also include a proximal interface 34 for mating with the hub cap 22 and/or any of a variety of existing vascular catheters and connectors, as described below.

Figure 3A:
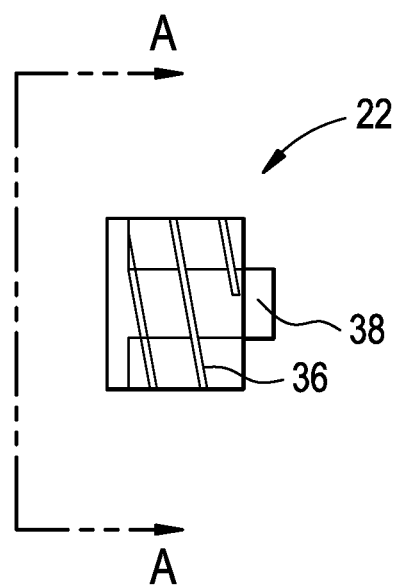
FIG. 3A is a side view of the catheter hub cap of the system of FIG. 1.
Figure 3B:
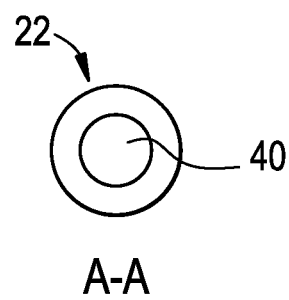
FIG. 3B is an end view of the catheter hub cap of FIG. 3A.

The hub cap 22 is shown in detail in FIGS. 3A-3B. The hub cap 22 can include a threaded interface 36 for mating with the proximal interface 34 of the catheter hub 26. The hub cap 22 can also include a male projection 38 configured to extend into and seal with the central lumen of the catheter hub 26. The hub cap can also take the form of a simple detachable sterile membrane that serves the purpose of preventing blood back-flow once the insertion needle has been withdrawn into the needle containment device, but that then, once the needle containment device has been detached, can be peeled away/detached to allow placement of, e.g., a Luer Lock or Insyte device. As shown, the integrated hub cap 22 can likewise have a uniform diameter and can permit withdrawal of the catheter insertion needle 18 without blood loss, thereby eliminating the need to immediately attach an intermediate cap device (e.g., a Luer-Lock® or Insyte® cap) when the catheter 24 is inserted. This can advantageously avoid blood loss, break in sterility, etc. This uniform diameter integrated hub sealing cap 22 can be removed after placement of the dressing assembly 14 if desired, and replaced with any standard Luer-Lock® or Insyte® type cap device. Alternatively, or in addition, this uniform diameter integrated hub sealing cap 22 can be constructed so that it can mate with all existing needle and needleless attachment systems. It may also be devised as part of a novel needleless attachment system.

The uniform-diameter hub cap 22 (uniform meaning, e.g., less than or equal to the diameter of the catheter hub and less than the diameter of the catheter hub flange) is shown removed from the catheter hub 26 in FIGS. 3A and 3B to demonstrate the attachment mechanism as well as the relative shape and diameter of each component that allows for the overall uniform diameter of the mated hub cap 22 and snap-fit catheter hub 26. It is this uniform diameter that can allow the snap-fit dressing assembly 14 to be mounted and slid into position over the hub cap 22 and snap-fit catheter hub 26 complex. The uniform outer diameter of the hub (excepting the mating features and stop flange) allows for the elimination of dead space between the catheter hub and the dressing channel in which the channel portion of the catheter hub is located. This feature can eliminate the accumulation of blood or other materials between the catheter hub and dressing hub channel that over time could serve to adversely affect sterility. FIG. 3B illustrates an end view of the hub cap 22 demonstrating the re-sealable mechanism 40 contained in the cap 22.

As shown in FIGS. 4A-4D, the catheter assembly 12 can also include a removable needle containment device 20 to which the hub cap 22 and/or the catheter hub 26 can be pre-mounted. The illustrated needle containment device 20 is can be in the form of an elongate telescoping tube. The tube can include a plurality of segments having a progressively increasing diameter and having gaskets or other sealing members positioned therebetween to form a single contiguous sealed interior chamber within the needle containment device 20. Each of the segments can be provided with a stop flange to prevent separation of the segments during extension of the needle containment device. The needle containment device can be formed from any of a variety of medical grade materials known in the art, including plastic, rubber, metal, and/or combinations thereof.

The insertion needle 18 can be withdrawn from the catheter 24 and catheter hub sealing cap 22 after successful placement of the catheter 24 in the patient's blood vessel. The needle 18 can be integrated with the safety needle containment device 20 in such a way that the withdrawn needle 18/needle containment device 20 (withdrawn from but still mechanically attached to the inserted catheter assembly 12) serves as a handle for use in mounting the sterile dressing assembly 14 to the inserted catheter assembly 12. After placement of the dressing assembly 14, the deployed needle containment device 20 with its contained needle 18 can be detached according to one of several possible mechanisms (e.g., a frangible portion or plastic breakaway). A snap-fit, threaded engagement, or similar reversible detachment feature can also be provided. Thus, once the dressing assembly 14 has been slid into place over the catheter 24 and snapped in place on the catheter hub 26 and the dressing deployed, this needle containment device 20 "handle" can be disconnected from the catheter hub 26 and/or the hub sealing cap 22. The needle containment device and hub cap can also be detached together as one unit, for example by unscrewing the hub cap from the catheter hub after dressing placement. A new hub cap can then be placed, or an existing "off the shelf" intermediate connector (e.g. Insight, Luer Lock) or IV line can be attached. The dressing assembly, at that point fully mounted and secured to the catheter, allows the catheter to be held firmly through the dressing assembly during this detachment-re-attachment process.

Figure 4A:
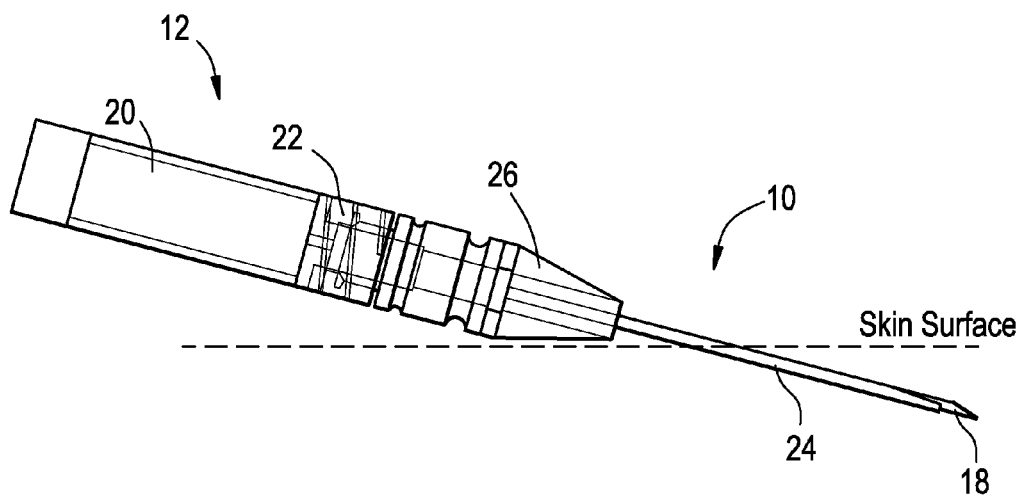
FIG. 4A is a side schematic view of the catheter assembly of the system of FIG. 1 inserted through a skin surface.
Figure 4B:
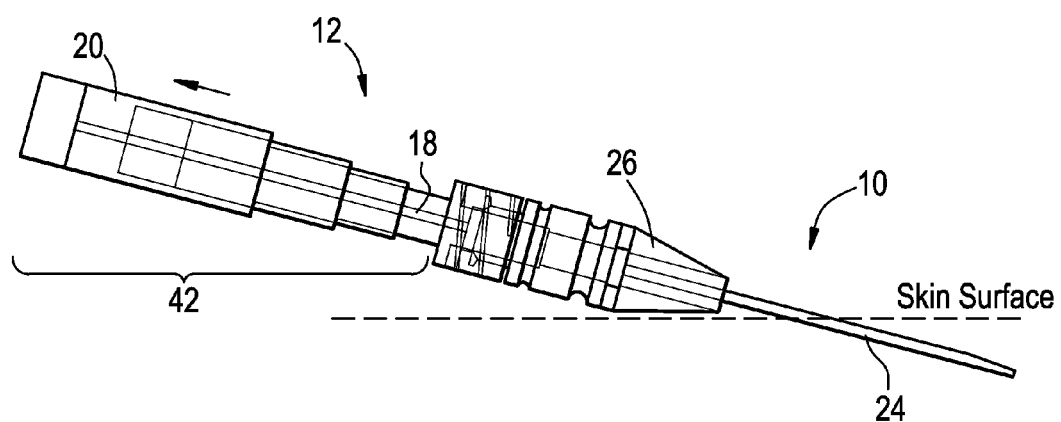
FIG. 4B is a side schematic view of the catheter assembly of FIG. 4A, shown with its needle containment device partially extended.
Figure 4C:
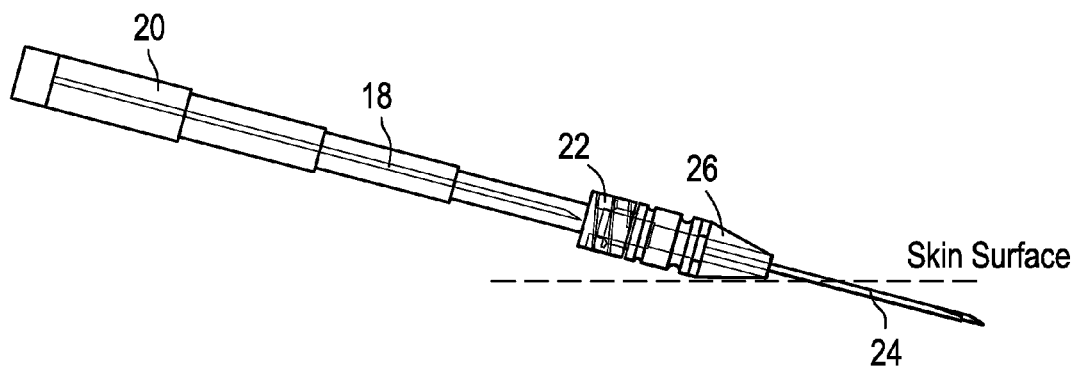
FIG. 4C is a side schematic view of the catheter assembly of FIGS. 4A-4B, shown with the needle containment device fully extended.
Figure 4D:
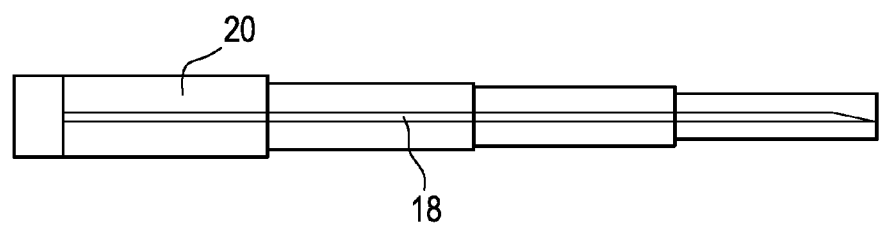
FIG. 4D is a side schematic view of the needle containment device, shown after having been separated from the catheter assembly of FIGS. 4A-4C.

In use, the catheter assembly 12 can be provided in sterile package in a pre-assembled configuration (e.g., with the insertion needle 18, needle containment device 20, hub cap 22, catheter hub 26, and catheter 24 assembled together). The insertion needle 18 can be used to pierce the patient's skin surface and to guide insertion of the catheter 24, as shown in FIG. 4A. As shown in FIG. 4B, a telescoping portion 42 of the needle containment device 20 can be extended to withdraw the insertion needle 18 proximally. The needle 18 remains entirely enclosed within the catheter-dressing system 10 during the process, thus allowing easy and safe withdrawal of the insertion needle 18 while preserving the necessary diameters of the system 10. Once the needle 18 is fully withdrawn from the catheter hub 26, as shown in FIG. 4C, the extended/deployed needle containment device 20 remains attached to the hub cap 22 and/or the catheter hub 26. The needle containment device 20 can then be used as a "handle" when subsequently mounting the dressing assembly 14, as explained below. After the dressing assembly 14 is snapped into position on the catheter hub 26, the "handle" formed by the needle containment device 20 and the needle 18 contained therein can be detached and safely discarded, as shown in FIG. 4D. The distal end of the needle containment device 20 can optionally include a tapered or conical distal portion to facilitate sliding of a dressing assembly from the needle containment device 20 onto the catheter hub 26 or hub cap 22. In other words, the needle containment device 20 can be shaped to ease the sliding of a dressing assembly disposed therearound distally onto the catheter hub and/or the catheter hub cap.

Figure 4E:
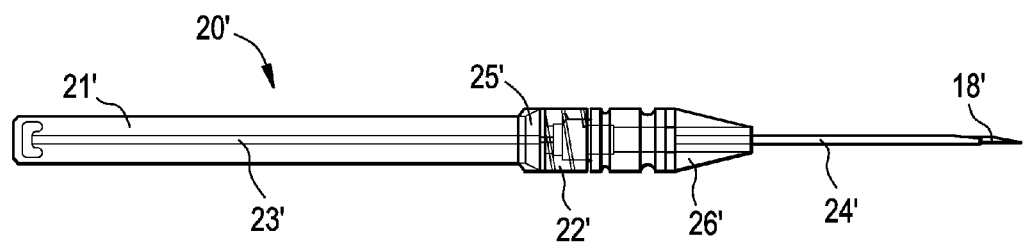
FIG. 4E is a side schematic view of an alternative embodiment of a needle containment device, shown coupled to a catheter assembly and with a slider in a distal, advanced position.
Figure 4F:
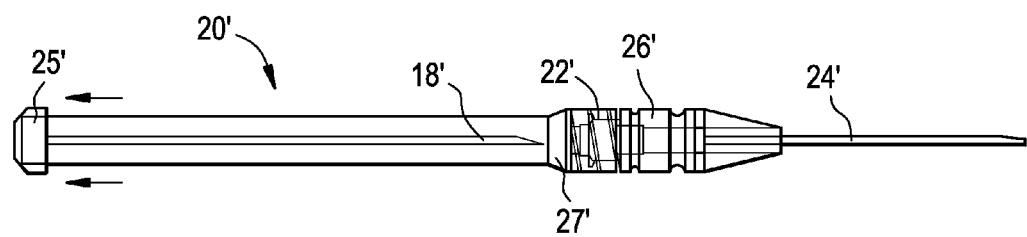
FIG. 4F is a side schematic view of the needle containment device and catheter assembly of FIG. 4E, shown with the slider in a proximal, retracted position.

FIGS. 4E-4F illustrate an alternative embodiment of a needle containment device 20' for facilitating removal and safe containment of the insertion needle 18' while providing a mounting handle for applying a sterile dressing assembly. As shown, the needle containment device 20' generally includes an elongate shaft 21' that defines a central lumen 23' sized to receive at least a portion of the insertion needle 18'. Preferably, the central lumen 23' can accommodate the entire insertion needle 18'. The needle containment device 20' also includes a slider 25' disposed therearound and coupled to the needle 18', for example via one or more struts that extend from the slider 25' radially inward towards the central lumen 23' through one or more longitudinal cut-out channels formed in the exterior of the elongate shaft 21'. In use, as shown in FIG. 4E, the slider 25' and the insertion needle 18' coupled thereto are placed in a distal, advanced position such that the needle 18' can guide insertion of the catheter 24'. Once the catheter 24' is inserted into a patient, or whenever otherwise desired, the slider 24' can be withdrawn or retracted proximally towards the position shown in FIG. 4F. As the slider 24' is pulled proximally along the longitudinal cut-out channels formed in the shaft 21', the needle 18' coupled thereto is withdrawn from the catheter 24' and catheter hub 26' and into the needle containment device. The slider can be locked into position by any of several mechanisms such as manual rotation past a specific check point.

The slider 25' can be coupled to an extendable sheath disposed within the shaft 21' and extending between the slider 25' and the distal end of the shaft 21'. Accordingly, as the slider 25' is withdrawn proximally, the sheath can extend over the longitudinal cut-out channels formed in the shaft 21', thereby encapsulating the needle 18' as it is withdrawn and preventing blood or other material from leaking through the cut-out channels. The sheath can be formed from a variety of flexible materials known in the art, such as latex, nitrile rubber, etc.

Like the embodiment of FIGS. 4A-4D, the embodiment of FIGS. 4E-4F can also act as a handle when placing a dressing assembly over the extended needle containment device 20', can be reversibly detachable from the catheter assembly, and can have a conical or tapered distal end 27' for guiding a dressing assembly from the needle containment device 20' over the catheter hub 26' or hub cap 22'.

Figure 4G:
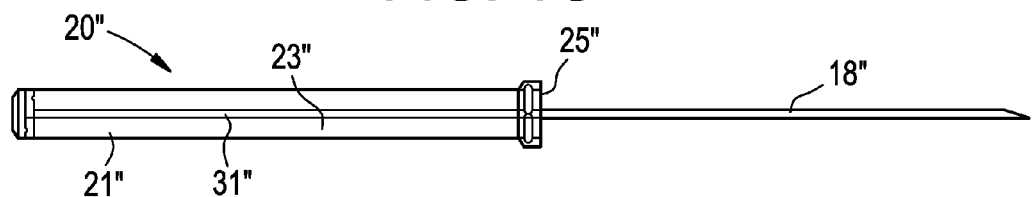
FIG. 4G is a side schematic view of another alternative embodiment of a needle containment device, shown with a needle in a deployed position.
Figure 4H:
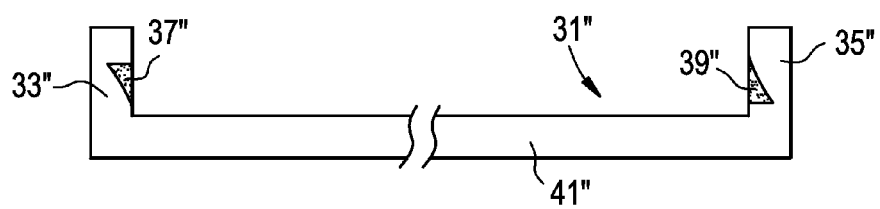
FIG. 4H is a schematic view of a cut-out channel formed in the needle containment device of FIG. 4G.
Figure 4I:
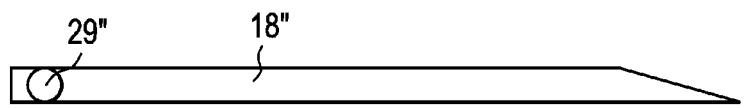
FIG. 4I is a cross-sectional side view of the needle of FIG. 4G having a slider coupled thereto via one or more struts.
Figure 4J:
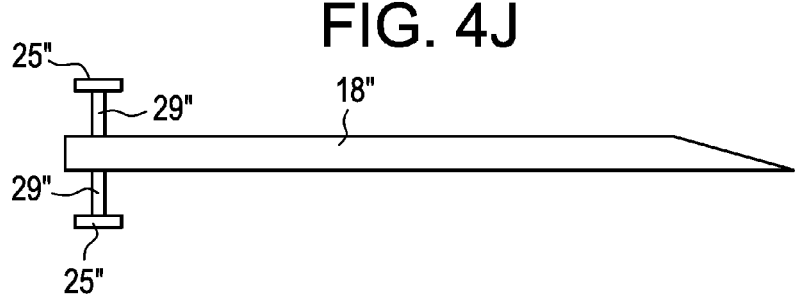
FIG. 4J is a top view of the needle, slider, and struts of FIG. 4I.

FIGS. 4G-4N illustrate another alternative embodiment of a needle containment device 20" for facilitating removal and safe containment of the insertion needle 18" while providing a mounting handle for applying a sterile dressing assembly. As shown, the needle containment device 20" generally includes an elongate shaft 21" that defines a central lumen 23" sized to receive at least a portion of the insertion needle 18". Preferably, the central lumen 23" can accommodate the entire insertion needle 18". The needle containment device 20" also includes a slider 25" coupled to the needle 18", for example via one or more struts 29" (shown in FIGS. 4I-4J) that extend from the slider 25" radially inward towards the central lumen 23" through one or more cut-out channels 31" formed in the exterior of the elongate shaft 21". As shown in FIG. 4H, the one or more channels 31" can include a main longitudinal portion 41" and proximal and/or distal right-angle spaces or side cuts 33", 35" into which the struts 29" can be rotated to lock a longitudinal position of the needle 18" relative to the elongate shaft 21". This lockout feature is augmented, in the illustrated embodiment, by proximal and distal unidirectional detents 37", 39" formed in the proximal side cut 33" and the distal side cut 35", respectively.

Figure 4K:
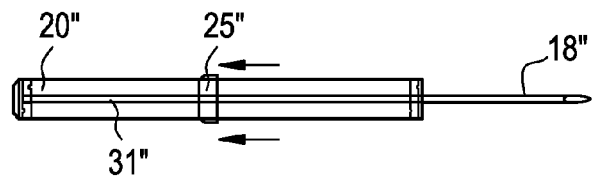
FIG. 4K is a side schematic view of the needle containment device of FIG. 4G shown with the needle in a partially deployed position.
Figure 4L:
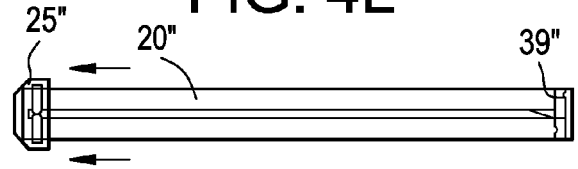
FIG. 4L is a side schematic view of the needle containment device of FIG. 4G shown with the needle in a fully retracted and locked position.
Figure 4M:
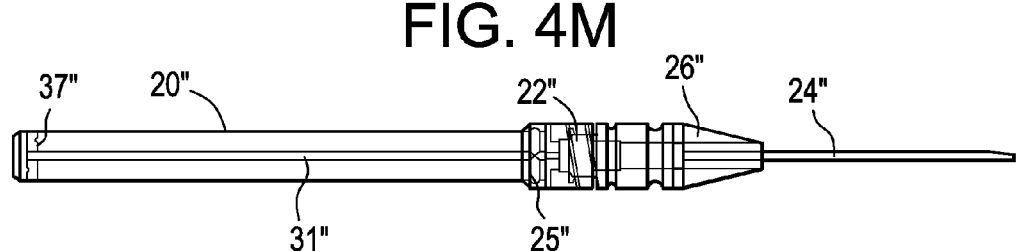
FIG. 4M is a side schematic view of the needle containment device and needle of FIG. 4G coupled to a catheter and catheter hub, the needle being shown locked in a deployed position.

In use, as shown in FIGS. 4G and 4M, the slider 25" and the insertion needle 18" coupled thereto are placed in a distal, advanced position such that the needle 18" can guide insertion of the catheter 24". In this position, the slider 25" can be placed in a first rotational orientation relative to the elongate body 21" such that a strut 29" coupled thereto is positioned within the distal side cut 35" of the channel 31". In this position, the distal detent 39" is effective to lock the slider 25" in position and prevent inadvertent longitudinal movement of the needle 18" relative to the needle containment device 20". Once the catheter 24" is inserted into a patient, or whenever otherwise desired, the slider 25" can be rotated to a second rotational orientation relative to the elongate body 21" (e.g., by applying sufficient force for the strut 29" to cam over and past the distal detent 39" and into the main longitudinal portion 41" of the channel 31"). When the slider 25" is so-positioned, the longitudinal position of the needle 18" relative to the needle containment device 20" can be freely adjusted, as shown in FIG. 4K.

Figure 4N:
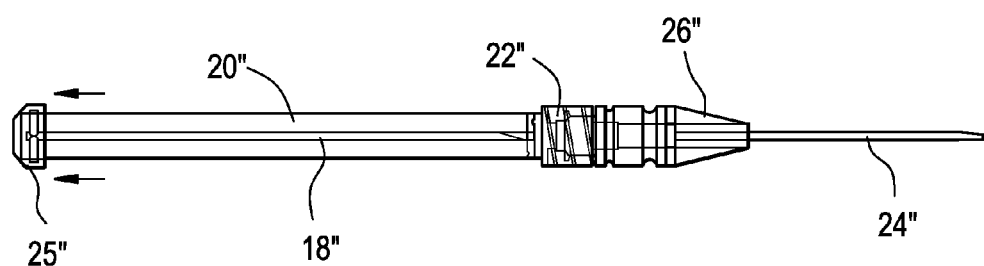
FIG. 4N is a side schematic view of the needle containment device and needle of FIG. 4G coupled to a catheter and catheter hub, the needle being shown locked in a retracted position.

Thus, the slider 25" can be withdrawn or retracted proximally towards the position shown in FIGS. 4L and 4N, withdrawing the needle 18" coupled thereto from the catheter 24" and catheter hub 26" and into the needle containment device 20". Once a strut 29" of the slider 25" is aligned with the proximal side cut 33" (e.g., when the needle 18" is fully contained within the needle containment device 20"'), the slider 25" can be rotated relative to the elongate body 21" to lock the needle 18" in the retracted position. For example, the slider 25" can be rotated to cause the strut 29" coupled thereto to cam over and past the proximal detent 37"', thereby locking the strut 29" within the proximal side cut 33" and preventing inadvertent longitudinal motion of the needle 18" relative to the needle containment device 20". The needle containment device 20" thus provides the option to lock the needle 18" into deployed or withdrawn positions by a sliding mechanism with a twisting unlock/lock mechanism. In one embodiment, this same turning motion can be used to disconnect the needle containment device from the catheter hub cap or the catheter hub once the catheter and sterile dressing have been deployed.

Figure 4O:
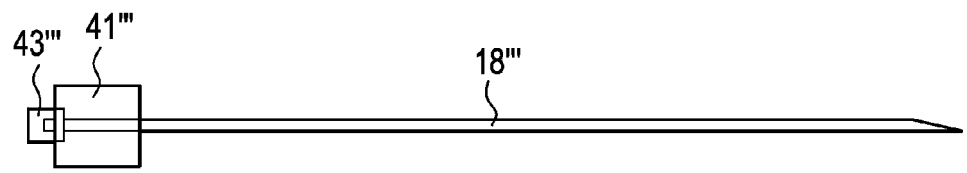
FIG. 4O is a schematic view of an insertion needle having a piston and filter coupled to a proximal end thereof.

FIGS. 4O-4T illustrate another alternative embodiment of a needle containment device 20"' for facilitating removal and safe containment of the insertion needle 18"' while providing a mounting handle for applying a sterile dressing assembly. As shown in FIG. 4O, the proximal end of the needle 18' can be fixedly mated to a piston 41'. A filter 43"' (e.g., an absorbent member formed from cotton or another sterile fabric) can be coupled to the piston 41"' at the proximal outlet of the needle 18"' such that blood flowing back through the needle 18"' will stain the filter 43' red, providing a visual indication to a user that the needle 18"' has been inserted into a blood vessel.

The illustrated needle containment device 20' generally includes an elongate shaft 21"' that defines a central lumen 23"' sized to receive the piston 41"', the filter 43"', and at least a portion of the insertion needle 18"'. Preferably, the central lumen 23"' can accommodate the entire insertion needle 18"'. The needle containment device 20' also includes a slider 25"' coupled to the needle 18', for example via one or more struts (not shown) that extend from the slider 25' radially inward towards the central lumen 23"' through one or more cut-out channels (not shown) formed in the exterior of the elongate shaft 21"'. The slider 25"' can optionally be sized to facilitate gripping by a user, and can include surface texturing or other features to enhance a user's grip. The slider 25' is configured to slide along an outer surface of the elongate shaft 21' to effect longitudinal movement of the needle 18"' relative to the needle containment device 20"'.

Figure 4P:
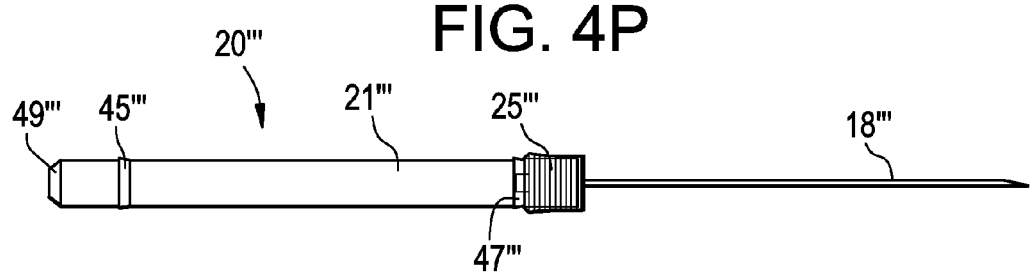
FIG. 4P is a side schematic view of another alternative embodiment of a needle containment device, shown with a needle in a deployed position.

The elongate shaft 21"' can optionally include surface features to restrict or resist movement of the slider 25' relative thereto. In the illustrated embodiment, the elongate shaft 21"' is provided with proximal and distal unidirectional locking projections 45"', 47"'. In use, the slider 25"'can be initially placed in a first position along the needle containment device 20"' in which the needle 18"' is deployed from the distal end of the needle containment device 20"', as shown in FIGS. 4P and 4S. When the slider 25' is so-positioned, the distal locking projection 47"' resists movement of the needle 18"' from the deployed position. In this deployed position, the needle 18" can guide insertion of the catheter 24"'. Once the catheter 24"' is inserted into a patient, or whenever otherwise desired, the slider 25' can be pulled proximally with sufficient force for the slider 25"' to deflect or cam over the distal locking projection 47"'. The longitudinal position of the needle 18" relative to the needle containment device 20" can then be freely adjusted by sliding the slider 25"' between the proximal and distal locking projections 45"', 47"'.

Figure 4Q:
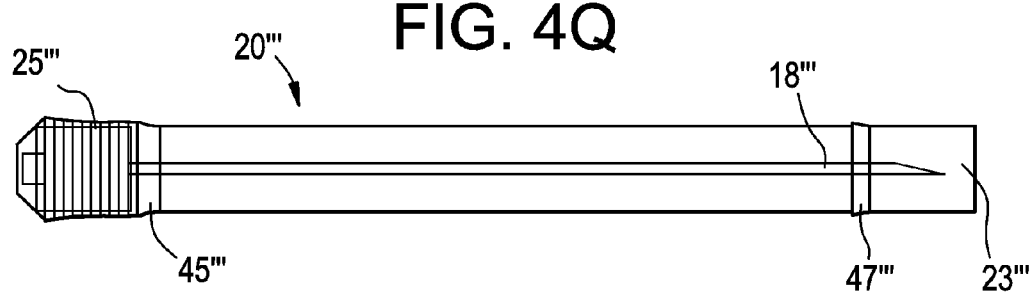
FIG. 4Q is a side schematic view of the needle containment device of FIG. 4P shown with the needle in a retracted position.
Figure 4R:
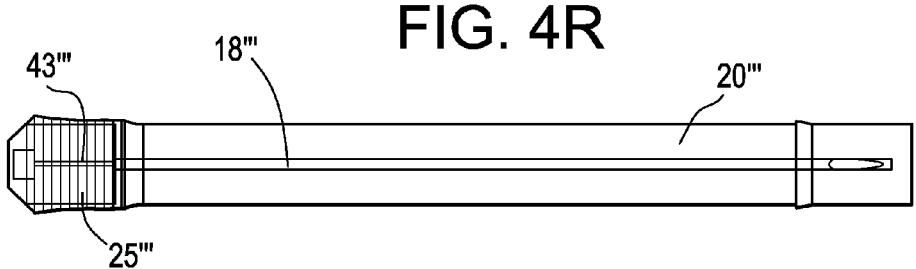
FIG. 4R is a side schematic view of a needle containment device having a slider, at least a portion of which is transparent to allow visualization of a filter contained therein.
Figure 4S:
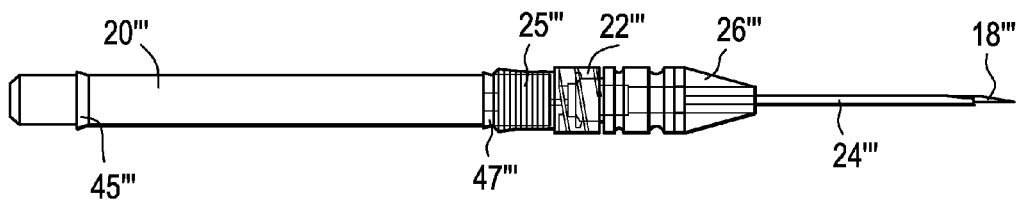
FIG. 4S is a side schematic view of the needle containment device and needle of FIG. 4P coupled to a catheter and catheter hub, the needle being shown locked in a deployed position.
Figure 4T:
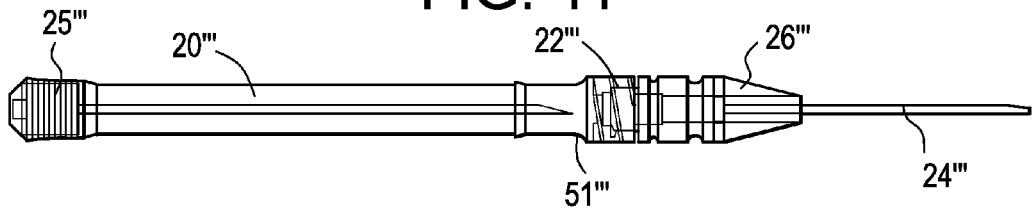
FIG. 4T is a side schematic view of the needle containment device and needle of FIG. 4P coupled to a catheter and catheter hub, the needle being shown locked in a retracted position.

Thus, the slider 25' can be withdrawn or retracted proximally towards the position shown in FIGS. 4Q and 4T, withdrawing the needle 18' coupled thereto from the catheter 24' and catheter hub 26"' and into the needle containment device 20"'. Once the slider 25' reaches the proximal locking projection 45"', (e.g., when the needle 18"' is fully contained within the needle containment device 20"'), the slider 25"' can be pulled proximally with sufficient force for it to deflect and/or cam over the proximal projection 45"' to lock the needle 18' in the retracted position. The needle containment device 20"' thus provides the option to lock the needle 18' into deployed or withdrawn positions by a sliding mechanism with an unlock/lock mechanism. As shown in FIG. 4R, at least a portion of the slider 25"' and/or the needle containment device 20"' can be transparent to allow visualization of the filter 43"' by a user, e.g., to confirm placement of the needle 18"' within a blood vessel by checking for blood staining of the filter 43"'. As shown particularly in FIG. 4T, the distal end of the needle containment device 20"' can include a flared portion 51"' to facilitate sliding of the dressing assembly over the needle containment device 20"' and onto the hub cap 22' or catheter hub 26"'.

Figure 5A:
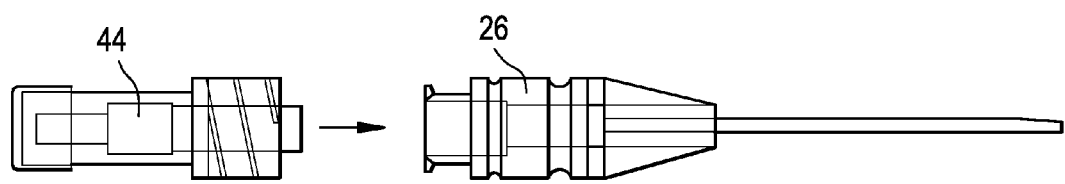
FIG. 5A is a side view of a Luer-Lock® cap and the catheter hub of the system of FIG. 1.
Figure 5B:
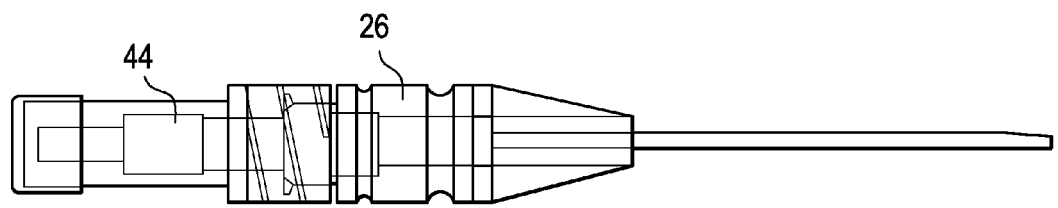
FIG. 5B is a side view of the Luer-Lock® cap and catheter hub of FIG. 5A coupled to each other.
Figure 5C:
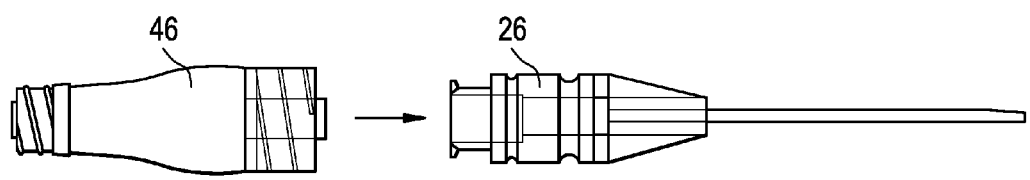
FIG. 5C is a side view of an Insyte® cap and the catheter hub of the system of FIG. 1.
Figure 5D:
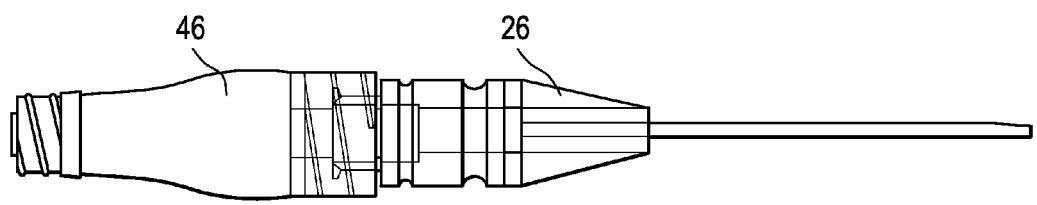
FIG. 5D is a side view of the Insyte® cap and catheter hub of FIG. 5C coupled to each other.

As noted above and shown in FIGS. 5A-5D, the catheter hub 26 can be configured to mate with any of a variety of standard connectors or components. FIGS. 5A and 5B illustrate attachment of a standard Luer-Lock® type connector 44 to the catheter hub 26. FIG. 5A shows the separate devices 26, 44 and FIG. 5B shows the connected devices 26, 44. FIGS. 5C and 5D illustrate attachment of a standard Insyte® type connector 46 to the catheter hub 26. FIG. 5C shows the separate devices 26, 46 and FIG. 5D shows the connected devices 26, 46.

Figure 6A:
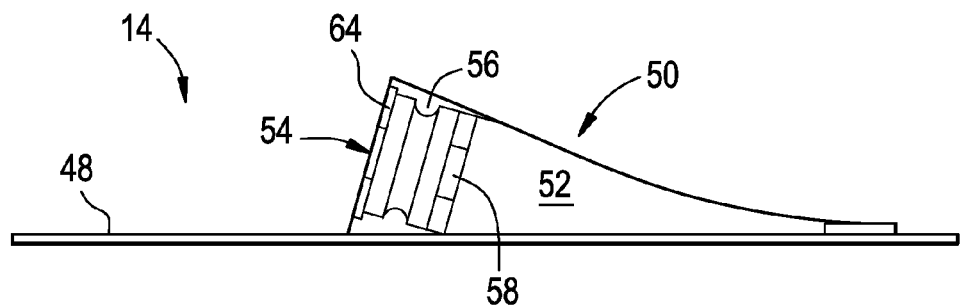
FIG. 6A is a side view the dressing assembly of the system of FIG. 1.
Figure 6B:
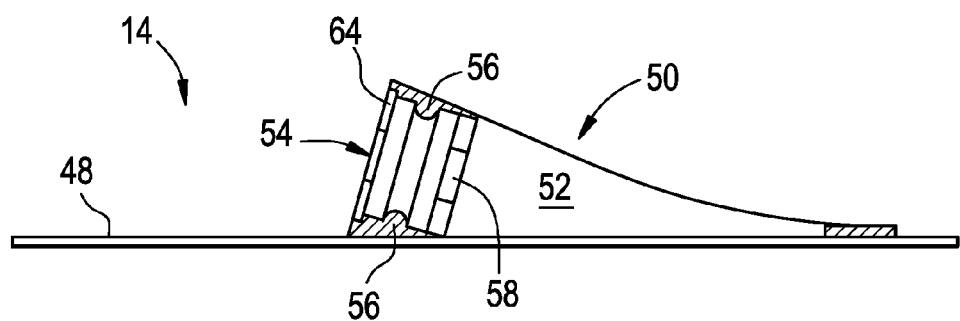
FIG. 6B is a longitudinal cross-sectional view of the dressing assembly of FIG. 6A.
Figure 6C:
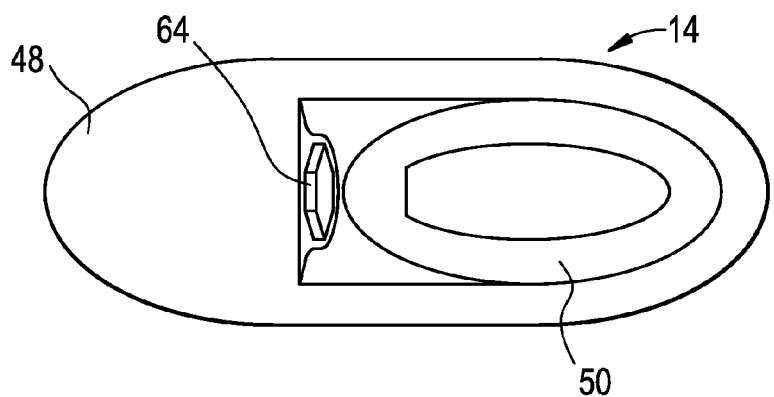
FIG. 6C is a top view of the dressing assembly of FIGS. 6A-6B.
Figure 6D:
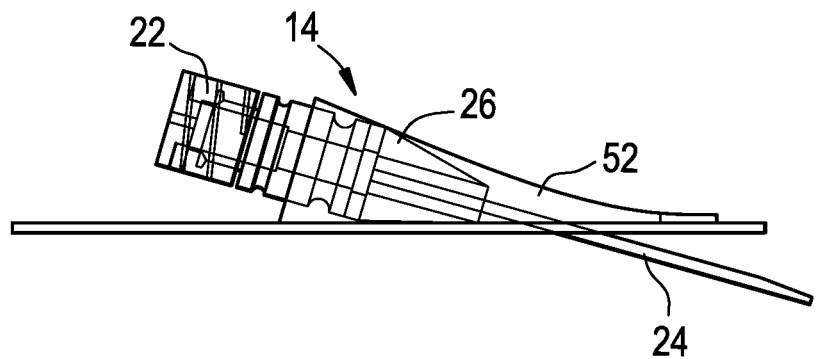
FIG. 6D is a side view of the dressing assembly of FIGS. 6A-6C installed around the catheter hub and the catheter of the system of FIG. 1, the dressing assembly being shown in phantom.
Figure 6E:
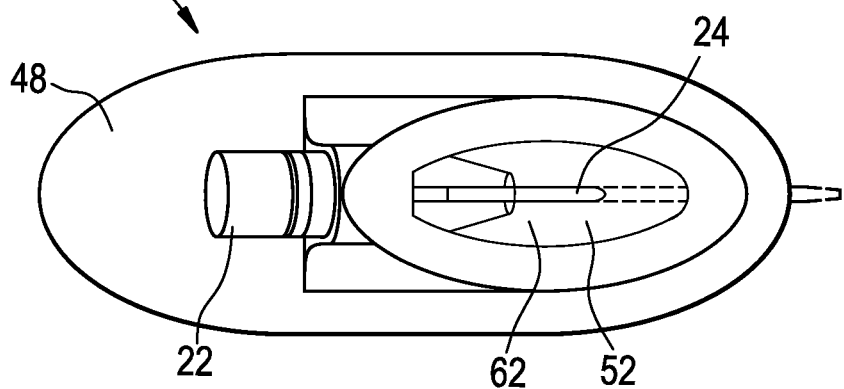
FIG. 6E is a top view of the dressing assembly, catheter hub, and catheter of FIG. 6D, a portion of the catheter being shown in phantom.

The dressing assembly 14 of the system 10 is shown in further detail in FIGS. 6A-6G. It will be appreciated that the dressing assembly 14, like any of the other structures or components described herein, can be used independently of the rest of the system 10, for example with "off the shelf" catheters and other devices. FIG. 6A illustrates a side view of the dressing assembly 14, FIG. 6B is a longitudinal cross-sectional view of the dressing assembly 14, and FIG. 6C is a top view of the dressing assembly 14. As shown, the dressing assembly 14 generally includes a base plate 48 configured to be adhered to a patient's skin and a body portion 50 extending upwards therefrom that defines an inner chamber 52. The dressing assembly 14 can also include a catheter hub receiving channel 54 extending from a proximal face of the dressing assembly 14 into the chamber 52. The hub receiving channel 54 can have a uniform diameter designed to receive the catheter hub 26 in a sliding fashion, leaving a minimum of dead space, and can include specific contour features designed to mate with the snap-fit catheter hub 26. For example, an annular male protrusion 56 can be provided within the hub receiving channel 54 and can be configured to snap-fit with the annular recess 28 formed in the catheter hub 26. As used herein, the term "snap-fit" refers to the "snapping" into position of the dressing assembly 14 over the catheter hub 26 into a final mating/sealing position. A "snap-fit" can also include audible and/or tactile feedback generated when the final mating/sealing position is reached, which can advantageously indicate to a user that the proper positioning has been achieved. A catheter securement stop flange mating site 58 can also be provided for receiving the stop flange 30 or the stop flange 30' formed on the catheter hub 26. When installed over an inserted catheter 24, as shown in FIGS. 6D-6E, the dressing assembly 14 can securely, sterilely, and circumferentially seal the catheter insertion site within the chamber 52. The hub receiving channel 54 can also be configured to form a sealing engagement with standard catheters and/or catheter cap/connection devices For example, a septum, O-ring, gasket, iris seal, gel seal, flap seal, or other sealing mechanism known in the art can be included within the hub receiving channel to form a sterile seal with components inserted therethrough.

The internal aspects of the dressing assembly 14 can be treated or coated with a sterilizing agent impregnated lining so that, during the mounting of the dressing over the catheter system, sterility can be maintained.

Figure 6F:
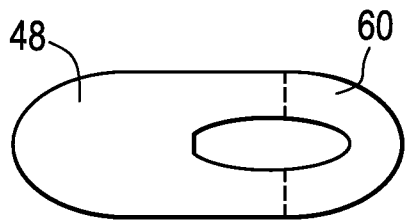
FIG. 6F is a top view of one embodiment of an adhesive pad of the dressing assembly of FIGS. 6A-6E.

The adhesive plate 48 of the dressing assembly 14 can optionally include a folding portion 60, as shown in FIG. 6F, to ease installation of the dressing assembly 14 over a catheter 24. Various parameters of the adhesive plate 48 can be adjusted to arrive at an optimal construction thereof relative to the rest of the dressing assembly 14 and the patient's body surface at the catheter-skin insertion site. For example, the size and shape of the adhesive plate 48 can be selected based on the body site chosen for catheter insertion. In addition, the composition of the adhesive plate 48, including the type of adhesive used, can be optimized. As the dressing assembly 14 can be designed to maintain catheter site sterility for a prolonged period, the adhesive used can be of the optimal type and grade to provide for such longer term fixation. Vacuum applied to the dressing complex through a specific channel can be used to further augment and maintain the sterile seal between the dressing and the skin at the attachment point.

Some or all of the dressing assembly 14 can be formed from a flexible material (e.g., soft or semi-soft silicone) to allow the dressing assembly 14 or parts thereof to conform to the patient's skin at the catheter insertion site during body surface movement. The dressing assembly 14 can also include an "easy-grip" cut out side profile, or similar intentional contour or surface texture alteration that allows for manual grasping and manipulation of the catheter hub 26 after the dressing assembly 14 has been placed, without disrupting the sterile seal. This easy-grip feature can also allow for the catheter hub 26 to be of the shortest length, while still meeting its sealing and securing specifications/requirements. This easy grip surface can be specifically designed with surface features that specifically aide in grasping and control of the dressing-catheter complex. As shown, the dressing assembly 14 can also have an ergonomic, low-profile shape that allows for (1) optimal positioning of the catheter 24 relative to the patient, (2) optimal adhesion of the plate 48, as well as maintenance of this adhesion (in response to body surface movement/changes), (3) optimal flexibility to allow movement with the static and/or changing contour of the body part into which the catheter 24 is placed, and (4) minimal catching on clothing, IV lines, or other devices with which the dressing-catheter system 10 might come into contact. The dressing assembly can be packaged in a folded position for the purpose of ease of mounting over the catheter assembly. Once in position on the catheter hub, the dressing assembly can then be unfolded and adhered in place on the patient's skin surface. The adhesive backing can be one of several possible arrangements that optimize the dressing-skin adhesion process. These arrangements can include, for example, a plurality of separate backing pieces that are peeled off sequentially as required. Functional members, such as backing extensions, or attached bodies such as strings, can aide in optimal peeling of the backing and application of the adhesive surface to the skin at the catheter-skin insertion site.

Figure 6G:
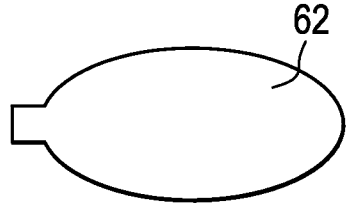
FIG. 6G is a top view of one embodiment of an access portal of the dressing assembly of FIGS. 6A-6F.

The dressing assembly 14, or any part thereof, can optionally be transparent or semi-transparent to permit visualization of the contained catheter hub 26 for the purpose of viewing the hub 26 and its connection to the dressing assembly 14 and/or viewing the hub's contents (e.g. when ensuring the adequacy of catheter flushing). Also, as shown in FIGS. 6E-6G, the dressing assembly 14 can include an access portal 62 (e.g., a re-sealable window apparatus that allows reversible access to the sterile chamber 52). The reversibly sealable access portal/window 62 can allow access to the sterile chamber 52 and the catheter insertion site for the purpose of maintaining catheter insertion site sterility. This window construction can include, for example, an adhesive film that can be peeled away from the dressing assembly 14 to open and allow access to the sterile chamber 52 and/or a flexible plastic sheet with a gasket-type snap-fit sealing mechanism. The access portal/window 62 can allow placement of—or have integrally attached—a material impregnated with a sterilizing agent. In use, the access portal 62 can be peeled away from the dressing assembly 14 to provide access to the sterile chamber 52. The access portal 62 can then be resealed to the dressing assembly 14, or can be discarded and replaced with a new access portal flap or cover. The illustrated access portal 62 substantially defines the entire upper surface of the chamber 52, however in other embodiments the access portal 62 can form only a portion of this surface, or can form or be located on other surfaces of the chamber 52.

The dressing assembly 14 can also include a second, injection-ready sealable portal to allow injection/introduction of sterilizing material/solution into the sterile chamber and/or catheter hub channel.

The dressing assembly 14 can also include an attachment and/or positioning mechanism for the hub protection device 16, which as described below can assist in maintaining the sterility of the catheter hub 26. The attachment mechanism can be formed at the external (or "working") end of the hub receiving channel 54 and can be in the form of an octagonal, hexagonal, ovoid, or other shape depression 64 similar to that used to receive the distal inner stop flange 30 at the internal end of the channel 54. This female mating point 64 can be designed to receive and stabilize the hub protection device 16.

Figure 7A:
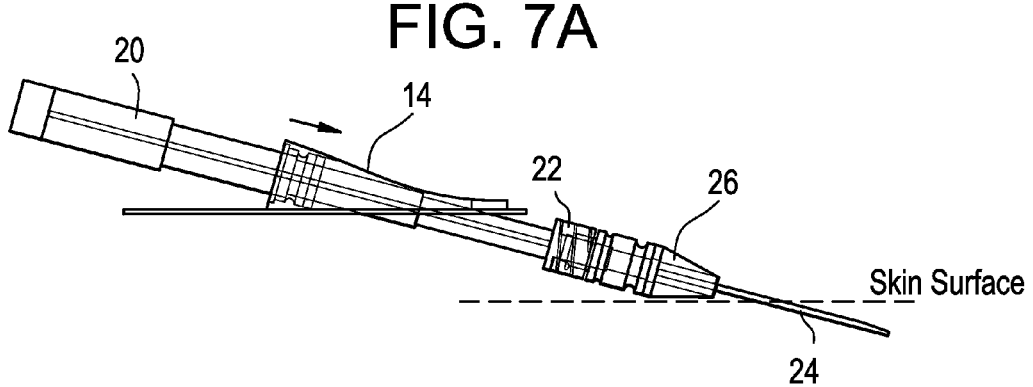
FIG. 7A is a side schematic view of the system of FIG. 1, shown with the catheter inserted through a skin surface, the needle containment device fully extended, and the dressing assembly partially advanced over the needle containment device.
Figure 7B:
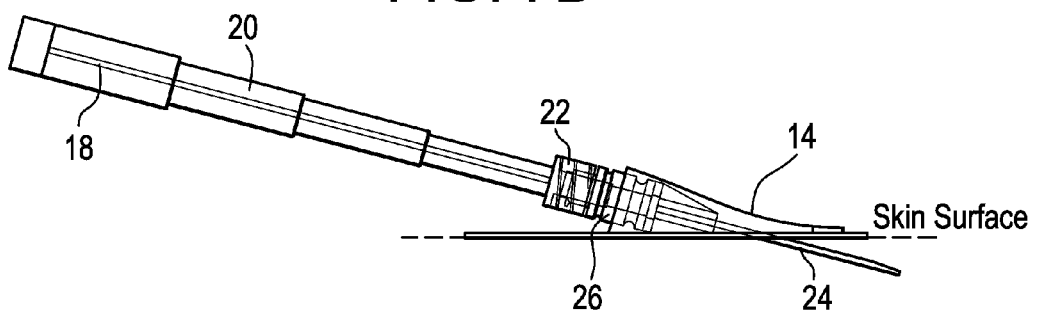
FIG. 7B is a side schematic view of the system of FIG. 7A, shown with the dressing assembly fully advanced over the catheter hub.
Figure 7C:
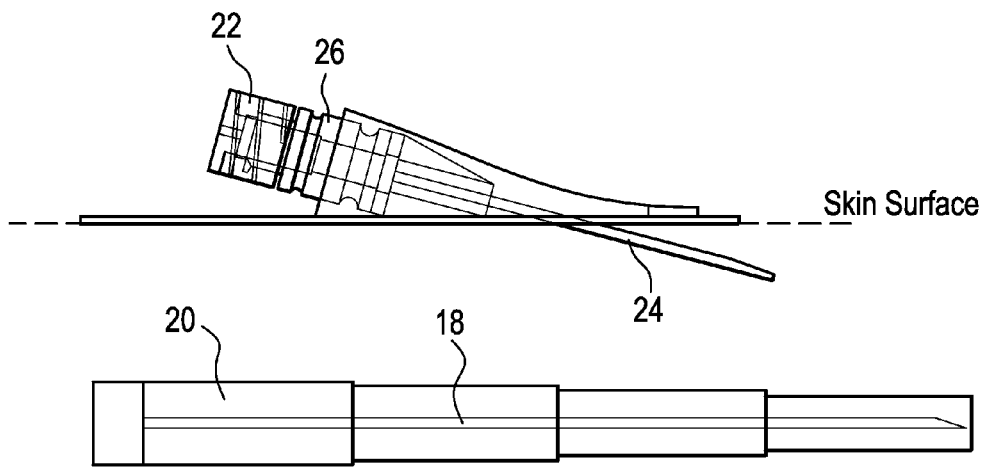
FIG. 7C is a side schematic view of the system of FIGS. 7A-7B, shown with the needle containment portion separated from the catheter assembly.

In use, as shown in FIG. 7A, the dressing assembly 14 can be slid over the fully extended and deployed (but still attached) needle securement device 20, said device 20 being used as a mounting "handle." As shown in FIG. 7B, the dressing assembly 14 can be advanced distally into its final position at the specified mating points on the snap-fit catheter hub 26. The dressing assembly 14 can then be mounted to the catheter hub 26 and adhered to the patient. Once the dressing assembly 14 is installed, the needle containment device 20 can be separated from the catheter hub 26 or hub cap 22, as shown in FIG. 7C.

In another exemplary use of the dressing assembly 14, a standard, "off the shelf" catheter and/or catheter hub cap device (e.g., Luer Lock, Insyte) can be coupled to the dressing, e.g., by inserting the inserted catheter hub/hub cap through the hub receiving channel 54, and then sliding the dressing distally over the catheter hub toward the skin insertion site to form a sealing engagement between the dressing assembly 14 and the catheter hub. Removal of the adhesive backing can form an adherence of the dressing assembly to the skin, thus forming a seal around the catheter-skin insertion site. If desired, the access portal 62 can be peeled back to expose the chamber 52 to allow for sterilization or other cleaning of the chamber, and can then be resealed to the dressing assembly 14 or replaced with a new cover flap.

As noted above, the dressing assembly 14 can also be used to dress and stabilize a variety of other devices, including arterial monitoring lines, access sheaths for intravascular procedures such as angiography and stenting, access sheaths for intravascular therapeutic devices such as intra-aortic balloon pumps and ventricular support devices, etc. These other devices can be of a standard type known in the art or can be customized as described above with respect to the catheter 24 and catheter hub 26 to enhance the sterility, security, and stability of the dressing-device seal. For example, such devices can be modified to include one or more custom stop flanges, recesses, snap-seal points, etc. It will be appreciated that the dressing assembly 14 can be slid over such devices either before or after they are inserted into a patient, and can also be used to manipulate such devices once they are inserted.

The dressing assembly 14 can also advantageously provide for hemostasis at an insertion site, preventing and/or containing the blood loss that normally occurs in connection with catheterization and other similar procedures in which the skin surface is punctured and/or a patient's vasculature is accessed. The dressing 14 can also be left in place after a procedure is completed and the catheter or other device is removed, in order to protect and maintain sterility at the insertion site during wound healing. For example, in one embodiment the dressing can be left in place for 6-8 hours after the completion of a procedure.

The dressing assembly 14 can also include a port through which a vacuum or pressure source can be coupled to the interior of the dressing assembly 14. For example, a vacuum can be applied to embodiments of the dressing 14 that are flexible in order to draw the flexible dressing taught against the skin surface and the implanted catheter, thereby further augmenting the stability of the dressing-catheter construct. In addition, a pressure source can be applied to the dressing to inflate a balloon disposed therein and/or coupled thereto. As the balloon is inflated, it can expand to substantially fill the interior of the dressing assembly 14 and exert pressure on a catheter disposed therein, thereby further stabilizing the catheter-skin junction. The balloon can also be inflated after the catheter is removed, to apply compression to the insertion site and thereby prevent blood loss and promote wound healing.

Figure 8:
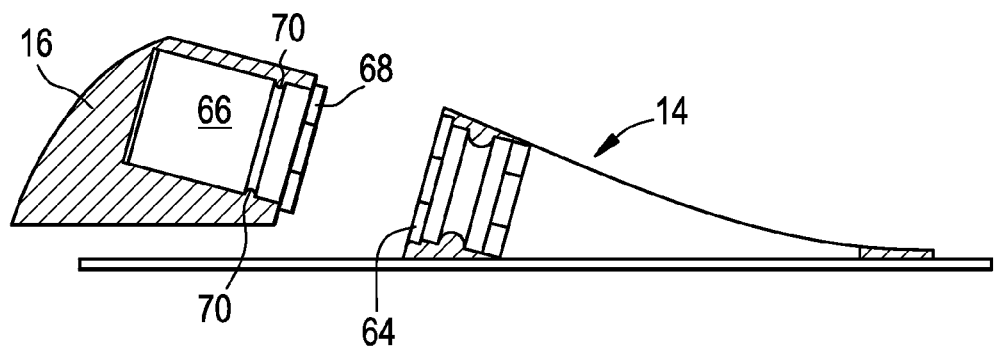
FIG. 8 is a longitudinal cross-sectional view of the hub protection device and dressing assembly of the system of FIG. 1.

As noted above, the system 10 can also include a hub protection device 16. As shown in FIG. 8, the hub protection device 16 is generally in the form of a cap having a bore 66 formed therein that is sized to receive the portion of the catheter hub 26 that protrudes from the dressing assembly 14 and/or the hub cap 22. The protection device 16 includes a male annular projection 70 that is configured to engage and/or snap-fit with the corresponding female recess 32 formed in the catheter hub 26 (see FIG. 2A). The protection device 16 also includes a mating feature 68 (also shown in FIG. 9A) that is configured to engage the corresponding mating feature 64 formed in the dressing assembly 14 (also shown in FIGS. 6A-6C and 9B).

Figure 9A:
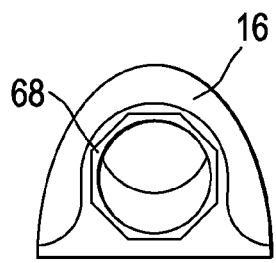
FIG. 9A is an end view of the hub protection device of FIG. 8.
Figure 9B:
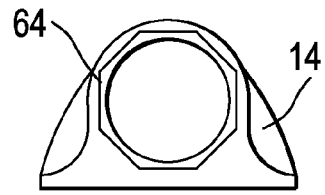
FIG. 9B is an end view of the dressing assembly of FIG. 8.
Figure 10A:
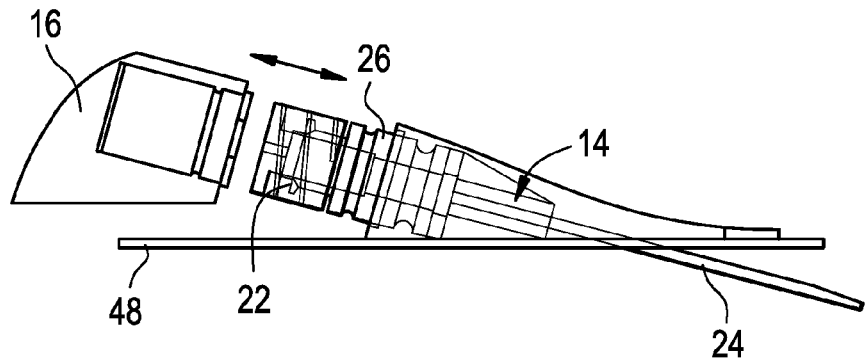
FIG. 10A is a side view of the hub protection device and dressing assembly of FIG. 8, the dressing assembly being shown installed over a catheter hub and a catheter insertion site.
Figure 10B:
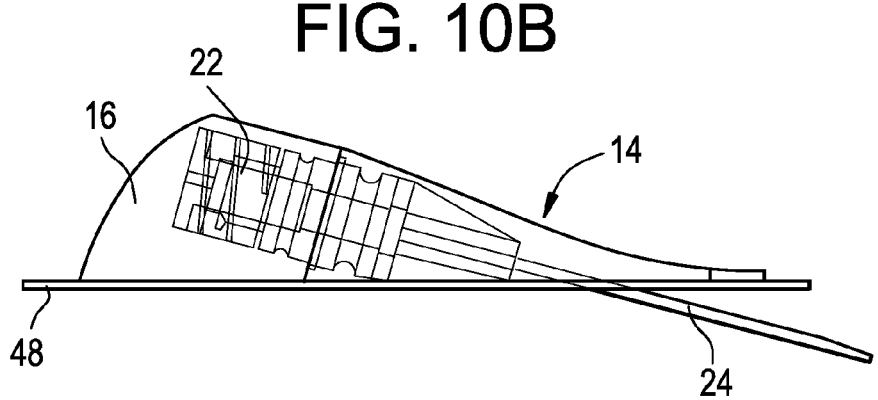
FIG. 10B is a side view of the hub protection device of FIG. 10A coupled to the dressing assembly and catheter hub of FIG. 10A.
Figure 10C:
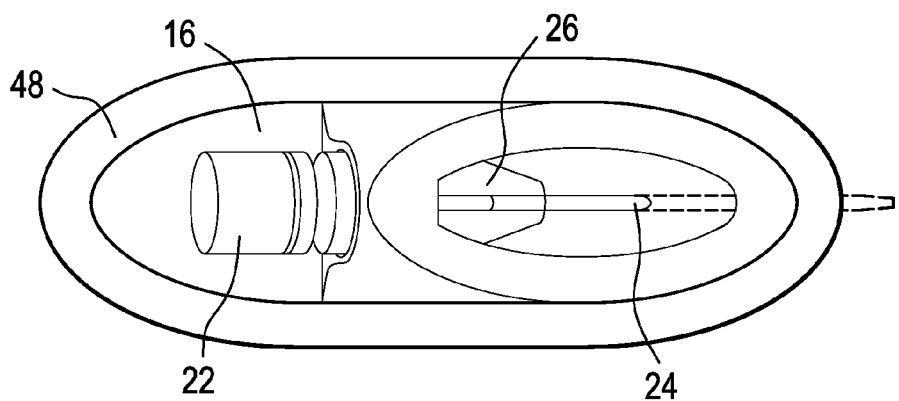
FIG. 10C is a top view of the hub protection device of FIG. 10A coupled to the dressing assembly and catheter hub of FIG. 10A.

In use, the hub protection device 16 of FIG. 9A and the dressing assembly 14 of FIG. 9B, as seen in these drawings, would be turned toward/facing each other and then pushed together over the snap-fit catheter hub 26 to achieve the final mated configuration. In other words, as shown in FIGS. 10A-10C, the hub protection device 16 can be installed over the protruding proximal end of the catheter hub 26 until it engages (e.g., snaps into) the installed catheter hub 26 and/or the installed dressing 14. Similar to the mating between the snap-fit catheter hub 26 and the snap-fit dressing assembly 14, the snap-fit hub protection device 16 can be secured by two separate but complimentary mating points: (1) the snap fit point between the hub protection device 16 and the catheter hub 26, and (2) the octagonal (or otherwise-shaped) male-female interface between the hub protection device 16 and the snap-fit dressing body 14.

The hub protection device 16, also called an "accessory catheter hub sterilizing and sealing protection device" can ergonomically cover and sterilely protect the working end of the capped intravascular catheter hub 26 (the end of the hub 26 that protrudes from the mounted sterile dressing assembly 14 and to which IV lines and other devices are attached). Use of the hub protection device 16 is entirely optional, and the system 10 can easily be used without the hub protection device 16.

As noted above, the circumferential snap-fit groove 32 in the catheter hub 26 can be designed (e.g., by being narrower than the subsequent "downstream" dressing snap-fit groove 28) to prevent "premature" attachment of the dressing assembly 14 to the first groove 32 as the dressing assembly 14 is slid over the catheter hub 26 into its final installed position.

The hub protection device 16 can also include a lining material that is impregnated with an anti-microbial and/or antibiotic cleansing/sterilizing solution so that mounting of the protective cap 16 serves to preserve the hub 26 in a ready-to-use clean/sterile state. Thus, when the device 16 is removed, the hub 26 does not need to be wiped with alcohol prior to use. The entire opposing surface of the hub protection device 16 can be treated in such a manner, or only certain parts such as the catheter hub channel 66. Similarly, any portion of the dressing (e.g., the hub receiving channel or the sterile chamber) can be lined with an antibiotic and/or antimicrobial cleansing/sterilizing material.

In one embodiment, the hub protection device 16 can have a shape that provides a smooth simple arc or other "non-catching" shape when attached to the dressing assembly 14, which can advantageously stabilize the catheter hub 26 against the base adhesive plate 48, support the catheter hub 26, and prevent or minimize the catching of clothing or other items on the catheter-dressing system 10. It will be appreciated that the hub protection device 16 can improve overall patient comfort and long term ease of use.

FIGS. 11A-11D show one exemplary embodiment of a protective cover that can be used with the catheter systems disclosed herein. The protective cover can be particularly useful when a patient is engaged in activities that would otherwise threaten the integrity of the catheter-dressing system, and/or with pediatric patients or patients with altered mental status. The protective cover can be applied over the dressing assembly and can be secured to the patient's body by various means appropriate to that body part. For example, an elastic arm band with a Velcro-type closure can be used when the dressing is applied to a patient's arm. The protective cover can protect the system and can also augment the integrity of the dressing assembly's adhesive seal. In one embodiment, the protective cover is formed from a rigid or semi-rigid plastic that is fit molded to the shape of the dressing assembly.

Figure 11A:
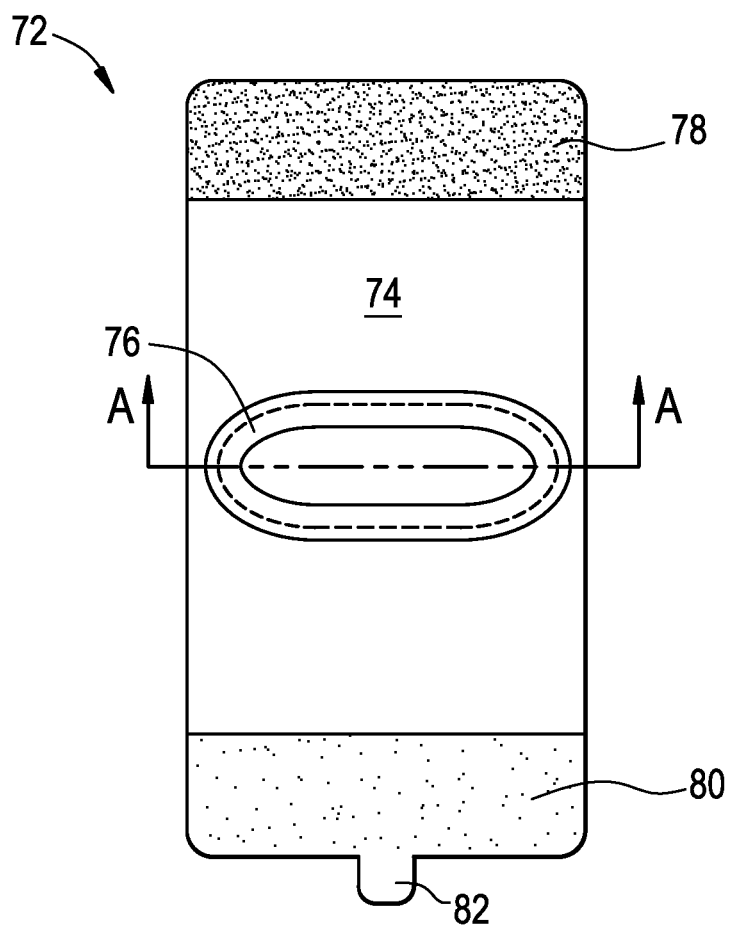
FIG. 11A is a top view of a protective cover.
Figure 11B:
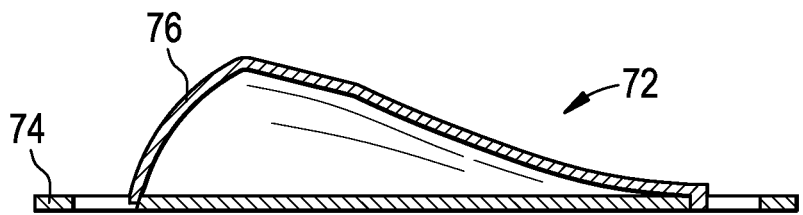
FIG. 11B is a cross-sectional view of the protective cover of FIG. 11A.
Figure 11C:
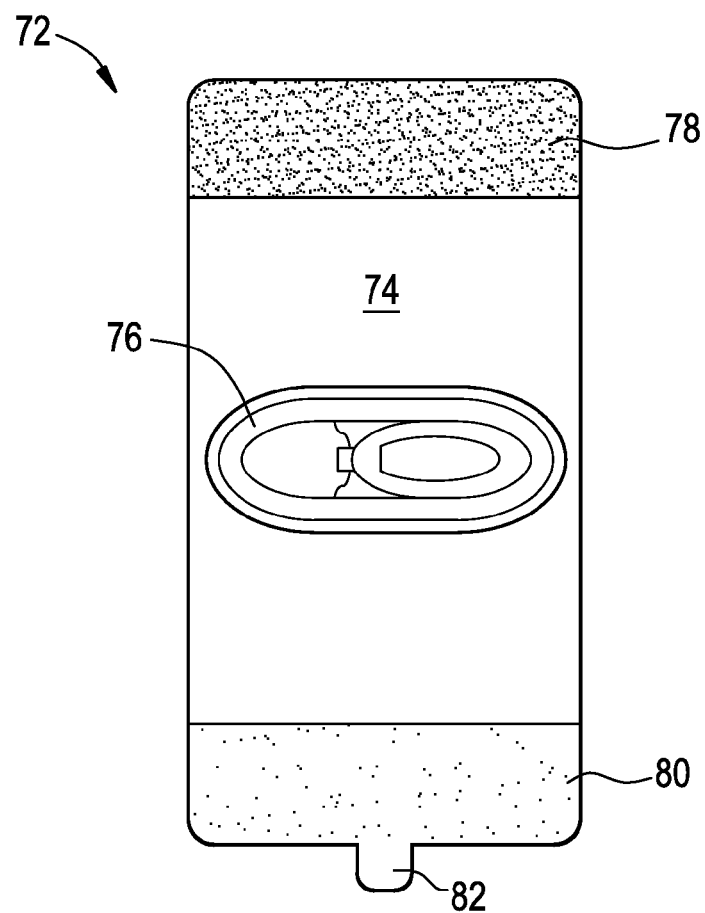
FIG. 11C is a top view of the protective cover of FIGS. 11A-11B installed over the system of FIG. 1.
Figure 11D:
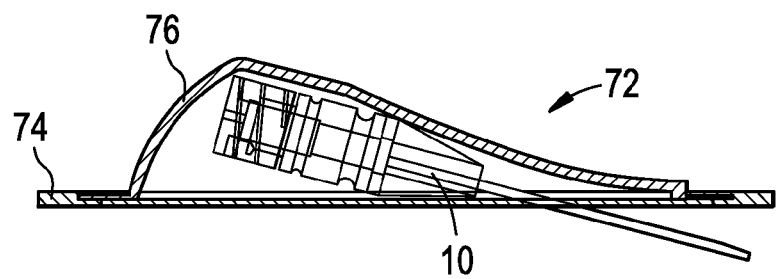
FIG. 11D is a cross-sectional view of the protective cover of FIGS. 11A-11C installed over the system of FIG. 1.

In the illustrated embodiment, the protective cover 72 is generally in the form of a flat sheet 74 that can be wrapped around an appendage of a patient and closed, sealed, and/or fastened to itself. As shown in FIGS. 11C-11D, the sheet 74 includes a raised portion 76 that can be molded to substantially conform to the exterior profile of an inserted catheter-dressing system 10. The sheet 74 also includes a hook region 78 and a loop region 80 which together form a hook and loop fastening system that allows the sheet 74 to be wrapped around a body part (e.g., an arm or a leg) and fastened to itself. A pull tab 82 can also be provided to facilitate separation of the hook and loop regions 78, 80. The protective cover can be formed from a stretchable and/or adhesive material, and can be provided in a variety of sizes, depending on the portion of the patient in which the catheter is inserted and the relative size of the patient. A skin-facing surface of the protective cover 72 can be coated with a sterilizing agent. Although a hook and loop fastening system is illustrated, any of a variety of attachment mechanisms known in the art can also be employed, such as adhesives, staples, sutures, magnets, friction-fittings, etc. In addition, while the illustrated embodiment of the protective cover 72 can be wrapped around a body part of a patient, the protective cover can also be designed to attach to a patient without wrapping around a body part.

The systems described herein can also be packaged in the form of a kit including dressings, catheters, hubs, hub caps, hub protection devices, insertion needles, needle containment devices, and/or other components of various sizes and shapes for use with various sized catheters, patients, body parts, etc. The kit can also include various items for sterile site preparation and sterile catheter insertion, such as tourniquets, preparation solutions, solution applicators, sterile saline flush, and/or sterile gloves. The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a caregiver immediately prior to a catheterization procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used device is obtained and if necessary cleaned. The device can then be sterilized. In one sterilization technique, the instrument is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical field.

It is preferred that the device is sterilized. This can be done by any number of ways known to those skilled in the art including beta or gamma radiation, ethylene oxide, steam, and/or a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A catheter system, comprising:
    a catheter assembly comprising an implantable catheter and a catheter hub formed at a proximal end of the implantable catheter;
    a needle containment device extending proximally from the catheter assembly, the needle containment device being coupled to an insertion needle disposed through an inner lumen of the implantable catheter; and
    a dressing assembly configured to slide over the catheter hub to form a circumferential seal around the catheter hub and a catheter insertion site;
    wherein the needle containment device is lockable in at least one of a first position in which the insertion needle coupled thereto is fully inserted through the implantable catheter and a second position in which the insertion needle is fully withdrawn from the implantable catheter, and
    wherein the needle containment device includes an elongate shaft and a slider, the slider being slidable relative to the elongate shaft and being coupled to the insertion needle such that the slider can be placed in a first position in which the insertion needle coupled thereto is fully inserted through the implantable catheter and a second position in which the insertion needle is fully withdrawn from the implantable catheter.

2. The catheter system of claim 1, wherein rotation of the slider relative to the elongate shaft is effective to lock the insertion needle in a fixed position relative to the needle containment device.

3. A catheter system, comprising:
    a catheter assembly comprising an implantable catheter and a catheter hub formed at a proximal end of the implantable catheter;
    a needle containment device extending proximally from the catheter assembly, the needle containment device being coupled to an insertion needle disposed through an inner lumen of the implantable catheter; and
    a dressing assembly configured to slide over the catheter hub to form a circumferential seal around the catheter hub and a catheter insertion site;
    wherein the needle containment device is lockable in at least one of a first position in which the insertion needle coupled thereto is fully inserted through the implantable catheter and a second position in which the insertion needle is fully withdrawn from the implantable catheter, and
    wherein the needle containment device includes a tapered distal end to facilitate sliding of the dressing assembly from the needle containment device onto the catheter hub.

4. The catheter system of claim 3, wherein the needle containment device has a diameter less than or equal to a diameter of the catheter hub and less than a diameter of a stop flange extending from the catheter hub.

5. A catheter system, comprising:
    a catheter assembly comprising an implantable catheter, a catheter hub formed at a proximal end of the implantable catheter, and a hub cap configured to be selectively coupled to a proximal end of the catheter hub;
    a needle containment device extending proximally from the catheter assembly, the needle containment device being coupled to an insertion needle disposed through an inner lumen of the implantable catheter; and
    a dressing assembly configured to slide over the catheter hub to form a circumferential seal around the catheter hub and a catheter insertion site,
    wherein the needle containment device is lockable in at least one of a first position in which the insertion needle coupled thereto is fully inserted through the implantable catheter and a second position in which the insertion needle is fully withdrawn from the implantable catheter.

6. The catheter system of claim 5, wherein the hub cap includes a reversibly-sealable membrane through which the insertion needle can be selectively passed without disrupting a fluid-tight seal across a proximal end of the hub cap.

7. The catheter system of claim 5, wherein the needle containment device is detachably connected to the hub cap.

8. The catheter system of claim 5, wherein the needle containment device is detachably connected directly to the catheter hub.

9. The catheter system of claim 5, wherein the dressing assembly comprises an adhesive base plate, a body portion, and a hub receiving channel formed in the body portion, the hub receiving channel being configured to form a sealing snap-fit engagement with the catheter hub when the catheter hub is disposed therein.

10. The catheter system of claim 5,
wherein the hub cap and the needle containment device each have a maximum diameter that is less than or equal to a maximum outer diameter of the catheter hub and less than a maximum outer diameter of a stop flange extending from the catheter hub.

11. The catheter system of claim 9, wherein the hub receiving channel of the dressing assembly includes an annular projection formed therein configured to form a sealing snap-fit engagement with a corresponding annular recess formed in the catheter hub.

12. The catheter system of claim 11, wherein the hub receiving channel of the dressing assembly includes a flange-receiving recess formed therein configured to mate with and seal to a corresponding stop flange formed on an exterior of the catheter hub.

13. The catheter system of claim 12, wherein a distance between the annular recess and the stop flange is less than a distance between the annular projection and the flange-receiving recess such that the stop flange exerts a compressive force on the flange-receiving recess when the dressing assembly is mated to the catheter assembly.

14. The catheter system of claim 12, wherein the stop flange is configured to prevent rotation of the catheter hub relative to the dressing assembly and to prevent the implantable catheter from being pulled out of the dressing assembly.

15. The catheter system of claim 12, wherein the stop flange has a cross-sectional dimension that is greater than a corresponding cross-sectional dimension of the hub receiving channel such that the stop flange prevents the catheter hub from being pulled proximally out of the dressing assembly.

16. The catheter system of claim 12, wherein the stop flange forms a seal with the flange-receiving recess and wherein the flange-receiving recess is located at a distal end of the hub receiving channel, adjacent to a sterile chamber of the dressing assembly.

17. A catheter system, comprising:
a catheter assembly comprising an implantable catheter and a catheter hub formed at a proximal end of the implantable catheter;
a needle containment device extending proximally from the catheter assembly, the needle containment device being coupled to an insertion needle disposed through an inner lumen of the implantable catheter;
a dressing assembly configured to slide over the catheter hub to form a circumferential seal around the catheter hub and a catheter insertion site; and
a hub protection device having a bore formed therein for receiving at least a portion of the catheter hub or a hub cap coupled to a proximal end of the catheter hub,
wherein the needle containment device is lockable in at least one of a first position in which the insertion needle coupled thereto is fully inserted through the implantable catheter and a second position in which the insertion needle is fully withdrawn from the implantable catheter.

18. The catheter system of claim 17, wherein the bore includes an annular projection formed therein configured to form a sealing snap-fit engagement with a corresponding annular recess formed in the catheter hub.

19. The catheter system of claim 18, wherein the hub protection device includes a distal projection configured to mate with a corresponding recess in the dressing assembly.

20. A catheter system, comprising:
a catheter assembly comprising an implantable catheter and a catheter hub formed at a proximal end of the implantable catheter;
a needle containment device extending proximally from the catheter assembly, the needle containment device being coupled to an insertion needle disposed through an inner lumen of the implantable catheter;
a dressing assembly configured to slide over the catheter hub to form a circumferential seal around the catheter hub and a catheter insertion site; and
a protective cover configured to further secure the dressing assembly to a patient and augment a sterile seal formed between the dressing assembly and the patient,
wherein the needle containment device is lockable in at least one of a first position in which the insertion needle coupled thereto is fully inserted through the implantable catheter and a second position in which the insertion needle is fully withdrawn from the implantable catheter.

21. A catheter system, comprising:
a catheter assembly comprising an implantable catheter and a catheter hub formed at a proximal end of the implantable catheter;
a needle containment device extending proximally from the catheter assembly, the needle containment device being coupled to an insertion needle disposed through an inner lumen of the implantable catheter; and
a dressing assembly configured to slide over the catheter hub to form a circumferential seal around the catheter hub and a catheter insertion site,
wherein the needle containment device is lockable in at least one of a first position in which the insertion needle coupled thereto is fully inserted through the implantable catheter and a second position in which the insertion needle is fully withdrawn from the implantable catheter, and
wherein the dressing assembly includes a vacuum port through which a vacuum can be applied to an interior volume of the dressing assembly.

22. A catheter system, comprising:
a catheter assembly comprising an implantable catheter and a catheter hub formed at a proximal end of the implantable catheter;
a needle containment device extending proximally from the catheter assembly, the needle containment device being coupled to an insertion needle disposed through an inner lumen of the implantable catheter; and
a dressing assembly configured to slide over the catheter hub to form a circumferential seal around the catheter hub and a catheter insertion site; and
a balloon disposed within the dressing assembly, the balloon being operatively coupled to an inflation lumen accessible from an exterior of the dressing assembly when the dressing assembly is mated to a skin surface,
wherein the needle containment device is lockable in at least one of a first position in which the insertion needle coupled thereto is fully inserted through the implantable catheter and a second position in which the insertion needle is fully withdrawn from the implantable catheter.

23. A catheter system, comprising:
a catheter assembly comprising an implantable catheter and a catheter hub formed at a proximal end of the implantable catheter;
a needle containment device extending proximally from the catheter assembly, the needle containment device being coupled to an insertion needle disposed through an inner lumen of the implantable catheter; and
a dressing assembly configured to slide over the catheter hub to form a circumferential seal around the catheter hub and a catheter insertion site;
wherein the needle containment device is lockable in at least one of a first position in which the insertion needle coupled thereto is fully inserted through the implantable catheter and a second position in which the insertion needle is fully withdrawn from the implantable catheter, and
wherein the dressing assembly comprises:
an adhesive plate configured to attach to the skin of a patient, the adhesive plate including an aperture through which at least a portion of the catheter assembly can be received;
a body portion fixedly attached to the adhesive plate, the body portion including a proximal opening configured to be circumferentially sealed to the catheter assembly; and
a resealable and replaceable flap portion coupled to the body portion and configured to be selectively peeled away from and attached to the body portion;
wherein the body portion and the flap portion together define a sterile sealed chamber with a skin surface of the patient when the dressing assembly is adhered thereto.

24. The dressing assembly of claim 23, wherein the flap portion provides an access portal for accessing the sterile sealed chamber.

* * * * *